(12) United States Patent
Chuang

(10) Patent No.: US 8,784,115 B1
(45) Date of Patent: Jul. 22, 2014

(54) ATHLETIC TRAINING OPTIMIZATION

(71) Applicant: Thomas Chu-Shan Chuang, San Francisco, CA (US)

(72) Inventor: Thomas Chu-Shan Chuang, San Francisco, CA (US)

(*) Notice: Subject to any disclaimer, the term of this patent is extended or adjusted under 35 U.S.C. 154(b) by 0 days.

(21) Appl. No.: 13/931,370

(22) Filed: Jun. 28, 2013

Related U.S. Application Data

(63) Continuation of application No. 13/842,124, filed on Mar. 15, 2013, which is a continuation-in-part of application No. 13/758,731, filed on Feb. 4, 2013.

(60) Provisional application No. 61/595,026, filed on Feb. 4, 2012.

(51) Int. Cl.
| | | |
|---|---|---|
| *G09B 3/00* | (2006.01) | |
| *A63B 24/00* | (2006.01) | |
| *G06F 17/40* | (2006.01) | |
| *A61B 5/11* | (2006.01) | |
| *A61B 5/024* | (2006.01) | |
| *G06F 17/30* | (2006.01) | |
| *G06F 19/00* | (2011.01) | |
| *A61B 5/00* | (2006.01) | |

(52) U.S. Cl.
CPC ......... *A63B 24/0062* (2013.01); *A63B 2225/20* (2013.01); *G06F 17/40* (2013.01); *A63B 24/0075* (2013.01); *A61B 5/1112* (2013.01); *A61B 5/02438* (2013.01); *G06F 17/30764* (2013.01); *A61B 2562/0219* (2013.01); *G06F 19/36* (2013.01); *A61B 5/411* (2013.01); *G06F 19/3475* (2013.01); *G06F 19/3481* (2013.01); *A63B 2225/50* (2013.01)
USPC ........... 434/326; 434/236; 434/238; 600/300; 600/301; 705/2; 705/3; 706/14

(58) Field of Classification Search
CPC ........... A63B 24/0062; A63B 2225/50; A63B 24/0075; A63B 2225/20; A63B 2230/06; A63B 2230/04; A63B 71/0686; A63B 2024/0065; A63B 24/00; A63B 2220/30; A63B 71/06; A63B 2220/12; A63B 2220/836; G06F 19/3481; G06F 19/3475; G06F 17/40; G06F 19/36; G06F 17/30764; A61B 5/222; A61B 5/411; A61B 5/02438; A61B 2562/0219; A61B 5/1112
USPC ........... 434/236, 238; 600/300, 301; 705/2, 3; 706/14

See application file for complete search history.

(56) References Cited

U.S. PATENT DOCUMENTS

| | | | | |
|---|---|---|---|---|
| 6,450,922 | B1* | 9/2002 | Henderson et al. | 482/8 |
| 6,736,759 | B1* | 5/2004 | Stubbs et al. | 482/8 |
| 2003/0013072 | A1* | 1/2003 | Thomas | 434/247 |
| 2003/0224337 | A1* | 12/2003 | Shum et al. | 434/247 |
| 2004/0102931 | A1* | 5/2004 | Ellis et al. | 702/188 |
| 2004/0147850 | A1* | 7/2004 | Amano et al. | 600/513 |
| 2004/0260191 | A1* | 12/2004 | Stubbs et al. | 600/520 |
| 2005/0070809 | A1* | 3/2005 | Acres | 600/508 |
| 2007/0197274 | A1* | 8/2007 | Dugan | 463/7 |

(Continued)

FOREIGN PATENT DOCUMENTS

WO     WO2010126825 A1    11/2010

*Primary Examiner* — Jack Yip
(74) *Attorney, Agent, or Firm* — Chuang Intellectual Property Law

(57) ABSTRACT

Methods and apparatuses for athletic training optimization are disclosed. In one example, a fitness level change is identified. In one example, a current training intensity is updated to reflect an updated user fitness level.

14 Claims, 18 Drawing Sheets

(56) References Cited

U.S. PATENT DOCUMENTS

| | | |
|---|---|---|
| 2007/0219059 A1* | 9/2007 | Schwartz et al. .................. 482/8 |
| 2007/0232451 A1* | 10/2007 | Hanoun ............................ 482/1 |
| 2007/0239479 A1* | 10/2007 | Arrasvuori et al. ................ 705/2 |
| 2009/0069156 A1* | 3/2009 | Kurunmaki et al. .............. 482/9 |
| 2009/0192391 A1* | 7/2009 | Lovitt et al. .................... 600/483 |
| 2009/0269728 A1* | 10/2009 | Verstegen et al. ............. 434/247 |
| 2009/0275442 A1* | 11/2009 | Nissila .............................. 482/4 |
| 2009/0312658 A1* | 12/2009 | Thieberger et al. ........... 600/520 |
| 2010/0292600 A1* | 11/2010 | Dibenedetto et al. ......... 600/520 |
| 2011/0125063 A1* | 5/2011 | Shalon et al. ................. 600/590 |
| 2011/0190646 A1* | 8/2011 | Kato et al. .................... 600/500 |
| 2011/0275940 A1* | 11/2011 | Nims et al. .................... 600/483 |
| 2012/0010478 A1* | 1/2012 | Kinnunen et al. ............. 600/301 |
| 2012/0253484 A1* | 10/2012 | Burich et al. ................... 700/91 |
| 2012/0254934 A1* | 10/2012 | McBrearty et al. ........... 725/118 |
| 2012/0283855 A1 | 11/2012 | Hoffman et al. |
| 2012/0290109 A1* | 11/2012 | Engelberg et al. .............. 700/91 |
| 2013/0041590 A1* | 2/2013 | Burich et al. ................... 702/19 |
| 2013/0066449 A1* | 3/2013 | Verstegen et al. .............. 700/91 |
| 2013/0171599 A1* | 7/2013 | Bleich et al. ................. 434/247 |
| 2013/0228063 A1* | 9/2013 | Turner ............................ 84/612 |
| 2013/0228064 A1* | 9/2013 | Turner ............................ 84/612 |

* cited by examiner

| Current Race Time | | | Interval Pace | Threshold Pace | Marathon Pace | Easy Pace |
|---|---|---|---|---|---|---|
| 5k | 10k | Marathon | 1600m | Mile | Mile | Mile |
| . | . | . | . | . | . | . |
| . | . | . | . | . | . | . |
| . | . | . | . | . | . | . |
| . | . | . | . | . | . | . |
| . | . | . | . | . | . | . |
| 20:37 | 42:45 | 3:16:50 | 6:25 | 6:58 | 7:31 | 8:02-8:32 |
| 21:04 | 43:41 | 3:21:04 | 6:33 | 7:05 | 7:41 | 8:10-8:40 |
| 21:25 | 44:24 | 3:24:35 | 6:40 | 7:18 | 7:48 | 8:12-8:42 |
| 21:49 | 45:15 | 3:28:23 | 6:48 | 7:26 | 7:56 | 8:20-8:50 |
| 22:14 | 46:08 | 3:32:19 | 6:56 | 7:34 | 8:05 | 8:28-9:00 |
| 22:41 | 47:03 | 3:36:24 | 7:04 | 7:43 | 8:15 | 8:36-9:06 |
| 23:08 | 48:00 | 3:40:39 | 7:12 | 7:51 | 8:24 | 8:45-9:15 |
| 23:32 | 48:79 | 3:44:00 | 7:13 | 7:54 | 8:33 | 9:08-9:38 |
| 24:10 | 50:10 | 3:50:00 | 7:23 | 8:00 | 8:47 | 9:18-9:48 |
| . | . | . | . | . | . | . |
| . | . | . | . | . | . | . |
| . | . | . | . | . | . | . |
| . | . | . | . | . | . | . |
| . | . | . | . | . | . | . |

FIG. 4

| Pace Level (PL) | 5K Time | 10K Time | Half-Marathon Time | Marathon Time |
|---|---|---|---|---|
| . | . | . | . | . |
| . | . | . | . | . |
| . | . | . | . | . |
| . | . | . | . | . |
| . | . | . | . | . |
| 40 | 24:00 | 49:51 | 1:50:31 | 3:48:46 |
| 39 | 23:38 | 49:01 | 1:48:40 | 3:45:09 |
| 38 | 23:09 | 48:01 | 1:46:27 | 3:40:43 |
| 37 | 22:41 | 47:04 | 1:44:20 | 3:36:28 |
| 36 | 22:15 | 46:09 | 1:42:17 | 3:32:23 |
| 35 | 21:48 | 45:16 | 1:40:19 | 3:28:23 |
| 34 | 21:25 | 44:25 | 1:38:27 | 3:24:39 |
| 33 | 20:59 | 43:31 | 1:36:27 | 3:20:35 |
| 32 | 20:39 | 42:50 | 1:34:53 | 3:17:29 |
| . | . | . | . | . |
| . | . | . | . | . |
| . | . | . | . | . |
| . | . | . | . | . |
| . | . | . | . | . |
| . | . | . | . | . |

FIG. 5A

| Pace Level (PL) | Base Pace | Marathon Pace | Half Marathon Pace | 10K Pace | 5K Pace |
|---|---|---|---|---|---|
| . | . | . | . | . | . |
| . | . | . | . | . | . |
| . | . | . | . | . | . |
| . | . | . | . | . | . |
| . | . | . | . | . | . |
| 40 | 10:09-9:18 | 8:44 | 8:26 | 8:01 | 7:44 |
| 39 | 9:58-9:08 | 8:35 | 8:17 | 7:53 | 7:36 |
| 38 | 9:51-8:57 | 8:25 | 8:07 | 7:43 | 7:27 |
| 37 | 9:43-8:47 | 8:15 | 7:57 | 7:34 | 7:18 |
| 36 | 9:30-8:37 | 8:06 | 7:48 | 7:25 | 7:09 |
| 35 | 9:21-8:28 | 7:57 | 7:39 | 7:17 | 7:01 |
| 34 | 9:11-8:18 | 7:48 | 7:30 | 7:08 | 6:53 |
| 33 | 8:56-8:10 | 7:39 | 7:22 | 7:00 | 6:45 |
| 32 | 8:52-8:02 | 7:32 | 7:14 | 6:53 | 6:38 |
| . | . | . | . | . | . |
| . | . | . | . | . | . |
| . | . | . | . | . | . |
| . | . | . | . | . | . |
| . | . | . | . | . | . |
| . | . | . | . | . | . |

FIG. 5B

| Split | Time | Distance | Avg Pace | Avg HR | Max HR |
|---|---|---|---|---|---|
| 1 | 07:12.9 | 1 | 7:13 | 161 | 174 |
| 2 | 07:17.5 | 1 | 7:18 | 171 | 178 |
| 3 | 07:18.1 | 1 | 7:18 | 172 | 178 |
| 4 | 07:23.0 | 1 | 7:23 | 173 | 179 |
| 5 | 07:03.1 | 1 | 7:03 | 175 | 179 |
| 6 | 07:28.5 | 1 | 7:29 | 173 | 180 |
| 7 | 07:18.6 | 1 | 7:19 | 174 | 182 |
| 8 | 04:00.3 | 0.59 | 6:48 | 177 | 183 |
| Summary | 55:02.0 | 7.59 | 7:15 | 172 | 183 |

FIG. 6

| Tempo - Lake Merced at HR 172 | | | Workout Type: Running |
|---|---|---|---|
| Interval | 1 mi | 148 to 174 bpm | |
| Interval | 1 mi | 164 to 178 bpm | |
| Interval | 1 mi | 166 to 178 bpm | |
| Interval | 1 mi | 167 to 179 bpm | |
| Interval | 1 mi | 171 to 179 bpm | |
| Interval | 1 mi | 166 to 180 bpm | |
| Interval | 1 mi | 166 to 182 bpm | |
| Interval | 0.59 mi | 171 to 183 bpm | |

FIG. 7

| Date | Course/Workout | Time (Min) | Avg Pace | Avg HR |
|---|---|---|---|---|
| 04/19/12 | Lake Merced/Tempo at Marathon Pace | 55 | 7:15 | 176 |
| 05/31/12 | Lake Merced/Tempo at Marathon Pace | 50 | 7:19 | 174 |
| 06/28/12 | Lake Merced/Tempo at Marathon Pace | 50 | 7:13 | 168 |
| 07/12/12 | Lake Merced/Tempo at Marathon Pace | 55 | 7:15 | 172 |
| 07/19/12 | Lake Merced/Tempo at Marathon Pace | 55 | 7:13 | 169 |
| Summary | | | 7:15 | 172 |

FIG. 8

| Date | Course/Workout | Time (Min) | Avg Pace | Avg HR |
|---|---|---|---|---|
| 12/1/2012 | Lake Merced/Tempo at Marathon Pace | 50 | 8:20 | 172 |
| 12/9/2012 | Lake Merced/Tempo at Marathon Pace | 50 | 8:20 | 175 |
| 12/11/2012 | Lake Merced/Tempo at Marathon Pace | 50 | 8:20 | 173 |
| 12/20/2012 | Lake Merced/Tempo at Marathon Pace | 50 | 8:20 | 165 |
| 1/3/2013 | Lake Merced/Tempo at Marathon Pace | 50 | 8:20 | 160 |

FIG. 9

ATHLETIC TRAINING OPTIMIZATION

CROSS REFERENCE TO RELATED APPLICATIONS

The present application is a continuation application of U.S. patent application Ser. No. 13/842,124 for "Athletic Training Optimization", to Thomas C. Chuang, and filed on Mar. 15, 2013, which is a continuation-in-part application of U.S. patent application Ser. No. 13/758,731 for "Athletic Training Optimization," to Thomas C. Chuang, and filed on Feb. 4, 2013, which claims priority from Provisional Patent Application No. 61/595,026 entitled "Athletic Training Optimization," to Thomas C. Chuang, and filed Feb. 4, 2012, the entire disclosures of which are incorporated herein by reference for all purposes.

BACKGROUND OF THE INVENTION

Athletes are constantly trying to improve their performance at their chosen athletic activity. Performance is closely tied to the athlete's fitness level in athletic activities such as running, cycling, and swimming. As a result, methods and apparatuses for improving fitness levels in athletes are needed.

BRIEF DESCRIPTION OF THE DRAWINGS

The present invention will be readily understood by the following detailed description in conjunction with the accompanying drawings, wherein like reference numerals designate like structural elements.

FIG. 4 illustrates an excerpt of a lookup table utilized to determine training paces in one example.

FIGS. 5A and 5B illustrate excerpts of lookup tables utilized to determine training paces in a further example.

FIG. 6 illustrates a baseline run data.

FIG. 7 illustrates configuration of a pace update run utilizing the baseline run data shown in FIG. 6.

FIG. 8 illustrates stored user running activity used to select a baseline run.

FIG. 9 illustrates stored user running activity used to identify a fitness level change.

DESCRIPTION OF SPECIFIC EMBODIMENTS

Figure 1:
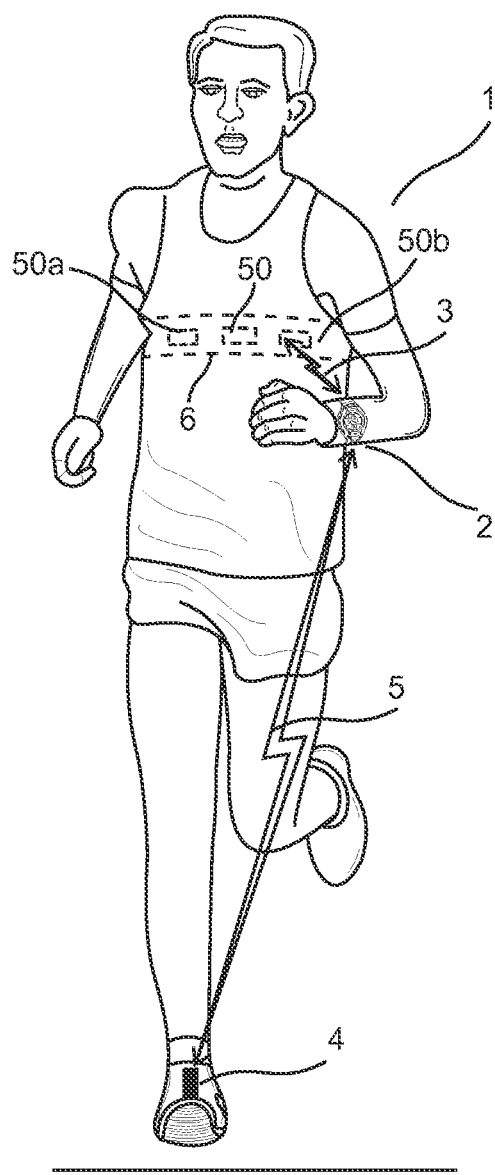
FIG. 1 illustrates a system for athletic performance monitoring being worn by a runner in one example.

Methods and apparatuses for athletic training optimization are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

For example, athletes often follow a training plan to prepare for an upcoming race in the hopes that they will run a faster time. Many training plans call for workouts to be performed at various paces. These paces are determined by the athlete's current fitness level. In order to make the most of their training, some measure of the athlete's current fitness level is needed so that the runner can train at the appropriate pace.

For example, in running, in the prior art, a lactate threshold test may be utilized to determine a runner's current fitness level (i.e., the user's lactate threshold pace). Other training paces may be generated from the results of the lactate threshold test using lookup tables as described herein. Lactate threshold testing is highly accurate in determining the user's lactate threshold pace. However, as a runner trains and improves or decreases fitness, the lactate threshold pace measured becomes outdated. Lactate threshold testing must be performed at a testing facility and is expensive. As a result, for most runners it is not practical to repeatedly use lactate threshold testing as a regular part of their training regimen to track the user's current fitness level.

Another technique discussed in the prior art to establish a current fitness level is for the runner to run a race at maximum effort and use the runner's performance to establish the runner's current fitness level. This technique is relatively inexpensive compared to a lactate threshold test. However, the inventor has recognized problems with using race times exclusively to establish the runner's current fitness level. For example, a runner may not wish to frequently race because of the effort and physical stress required for a peak performance. Furthermore, racing also interrupts the runner's training rhythm, as additional rest beforehand or recovery afterward may be needed. Furthermore, the accuracy of this method is predicated on the runner performing at a near peak level in order to gauge the runner's fitness level, which may be difficult or undesirable for the runner to repeatedly achieve each race.

The inventor has recognized that improved methods and apparatuses are needed for developing current, up-to-date workouts and training plans for athletes which optimize their training. In particular, improved apparatuses and methods are needed to monitor/determine an athlete's current fitness level so they can train at the correct intensity level (e.g., pace).

Because a runner's fitness level improves as he trains (or alternatively, decreases as the runner decreases training), methods and apparatuses are needed to monitor a runner's current fitness level. Furthermore, methods and apparatuses are needed to optimize a runner's training based on the runner's current fitness level.

In various embodiments described below, the methods described below may be implemented as sequences of instructions executed by one or more computers. The instructions may be incorporated into one or more application programs stored in a non-transitory computer readable storage memory of one or more computers, the one or more application programs which when executed by a computer cause the computer to perform the methods recited herein.

In one example, a fitness level monitoring method includes receiving a baseline data associated with a baseline activity, the baseline data comprising a heart rate (HR) data and a movement or pace data, receiving a training data associated with a plurality of training activities, and processing the training data to identify a need for a fitness test activity. The method includes receiving a fitness test data associated with a fitness test activity, and processing the baseline data and the fitness test data to identify a user fitness level change (i.e., determine a current fitness level). In one example, a computer readable storage memory stores instructions that when executed by a computer cause the computer to perform this recited method for fitness level monitoring.

In one example, the baseline activity is a baseline run. In a further example, the baseline activity is a baseline cycling activity or swimming activity or walking activity. In one example, the baseline data further includes navigation data. Where the swimming activity is in a pool, navigation data may include directional data operable to calculate number of laps swam.

In one example, a method for updating a current training pace includes storing a training data associated with a plurality of user activity, the training data including heart rate data and pace data. The method includes identifying a need for a training pace update activity, receiving an update data associated with a training pace update activity, and processing the update data to determine an updated current training pace. In one example, a computer readable storage memory stores instructions that when executed by a computer cause the computer to perform this recited method for updating a current training pace. In one example, the training data further includes navigation data.

In one example, the training pace update activity is a training pace update run. In a further example, the training pace update activity is a training pace update cycling activity or swimming activity.

In one example, a fitness level monitoring method includes receiving a baseline data associated with a baseline run, the baseline data comprising a navigation data, a heart rate data, and a pace data. The method includes receiving a fitness test data associated with a fitness test run. The method further includes processing the baseline data and the fitness test data to identify a user fitness level change. In one example, a computer readable storage memory stores instructions that when executed by a computer cause the computer to perform this recited method for fitness level monitoring.

In one example, a fitness level monitoring method includes receiving a baseline data associated with a baseline run, the baseline data comprising a navigation data, a heart rate data, and a pace data. The method includes receiving a training data associated with a plurality of training runs and processing the training data to identify a need for a fitness test run. The method includes receiving a fitness test data associated with a fitness test run, and processing the baseline data and the fitness test data to identify a user fitness level change. In one example, a computer readable storage memory stores instructions that when executed by a computer cause the computer to perform this recited method for fitness level monitoring. In one example, the user fitness level change is an improved fitness level.

In one example, the method further includes receiving a current training pace input by a user, wherein the user is prompted to run the baseline run at the current training pace. In one example, the method further includes determining an updated current fitness level training pace. In one example, determining an updated current fitness level training pace includes retrieving the heart rate data from the baseline data, receiving an update data associated with an update run, wherein during the update run the user is prompted to maintain a target heart rate, the target heart rate determined from the heart rate data from the baseline data, and processing the update data to determine an updated current training pace.

In one example, a method for updating a current training pace includes storing a training data associated with a plurality of user running activity, the training data comprising navigation data, heart rate data, and pace data. The method includes receiving an update data associated with a training pace update run, and processing the update data to determine an updated current training pace. In one example, a computer readable storage memory stores instructions that when executed by a computer cause the computer to perform this recited method for updating a current training pace.

In one example, a method for updating a current training pace includes storing a training data associated with a plurality of user running activity, the training data comprising navigation data, heart rate data, and pace data. The method includes identifying a need for a training pace update run, receiving an update data associated with a training pace update run, and processing the update data to determine an updated current training pace. In one example, a computer readable storage memory stores instructions that when executed by a computer cause the computer to perform this recited method for updating a current training pace.

In one example, during the training pace update run the user is prompted to maintain a target heart rate. For example, the target heart rate is determined from training data associated with a running activity in the plurality of user running activity. In one example, identifying a need for a training pace update run comprises determining an elapsed time from a previous training pace update run. In one example, identifying a need for a training pace update run comprises determining a user fitness level change (i.e., determine a current user fitness level). For example, determining a user fitness level change includes receiving a workout data associated with a workout running activity, and processing the workout data and the training data to determine a user fitness level change. In one example, processing the workout data and the training data includes identifying a running activity from the training data having a same navigation route and a same approximate pace as the workout running activity, and comparing a first heart rate data associated with the running activity and a second heart rate data associated with workout running activity.

In one example, the method further includes identifying a current start location of a user, and searching the training data associated with a plurality of user running activity to identify a user running activity having a same start location as the current start location. The method further includes prompting the runner during the training pace update run to run a route corresponding to the user running activity having a same start location as the current start location. For example, prompting the runner during the training pace update run comprises outputting turn by turn directions. For example, the turn by turn directions are voice communications output at a headset.

In one example, a system for training optimization includes a sensor configured to monitor a user heart rate data, a navigation system configured to monitor a user navigation data, the navigation data comprising user location data and user pace data, and a processor. The system further includes a memory configured to store a baseline data associated with a baseline run, a training data associated with one or more training runs, a fitness test data associated with a fitness test run, and a training optimization application configured to process the baseline data and the fitness test data to identify a user fitness level change.

In one example, the navigation system, processor, and memory are implemented at a body worn device. For example, the body worn device is a wrist-worn device or a smartphone. In one example, the system further includes a headset configured to receive and output audio prompts to a user.

In one example, a system for updating a training pace includes a sensor configured to monitor a user heart rate data, a navigation system configured to monitor a user navigation data, the navigation data comprising user location data and user pace data, and a processor. The system further includes a memory configured to store a training data associated with one or more training runs, an update data associated with a training pace update run, and a training optimization application configured to process the update data to determine an updated current training pace. In one example, the training optimization application is further configured to identify a need for a training pace update run.

In one example, the training optimization application is configured to process the navigation data to identify a current start location of the user, search the training data to identify a training run having a same start location as the current start location, and prompt the user during the training pace update run to run a route corresponding to the training run having a same start location as the current start location, wherein the training optimization application is further configured to prompt the user to maintain a target heart rate determined from the training run having a same start location as the current start location.

In one example, an apparatus for training optimization includes an interface configured to receive a user heart rate data, a navigation system configured to monitor a user navigation data, the navigation data comprising user location data and user movement or pace data, and a processor. The apparatus further includes a memory configured to store a baseline data associated with a baseline activity, a training data associated with one or more training activities, and a training optimization application configured to process the baseline data and the training data to identify a user fitness level change.

In one example, an apparatus for updating a training pace includes an interface configured to receive a user heart rate data, a navigation system configured to monitor a user navigation data, the navigation data comprising user location data and user pace data, and a processor. The apparatus includes a memory configured to store a training data associated with one or more training activities, an update data associated with a training pace update activity, and a training optimization application configured to process the update data to determine an updated current training pace.

In one example, a non-transitory computer readable storage memory stores instructions that when executed by a computer cause the computer to perform a method for athletic training. The method includes identifying a present start location of a user, processing a stored data to identify a workout for the user to perform, and receiving a training data associated with the workout during a performance of the workout by the user.

In one example, a method for athletic training includes receiving a first data associated with a first athletic activity performed at a training pace, the first data comprising a first heart rate data. The method includes receiving a second data associated with a second athletic activity performed at a target heart rate, the target heart rate associated with the first heart rate data, the second data comprising a pace data. The method further includes determining an updated training pace utilizing the second data. In one example, the athletic activity is a running activity. In a further non-limiting example, the athletic activity is a cycling activity, swimming activity, or walking activity.

In one example, a method for athletic training includes setting a training pace for a workout type, correlating a target heart rate to the workout type, and setting an updated training pace for the workout type responsive to receiving a data from an athletic activity corresponding to the workout type. In one example, the athletic activity is a running activity. In a further non-limiting example, the athletic activity is a cycling activity, swimming activity, or walking activity.

In one example, a method for athletic training includes receiving a plurality of training data associated with a plurality of training activities, wherein each training activity of the plurality of training activities is identified by a workout type. The method includes identifying the plurality of training data associated with a workout type, and processing the plurality of training data to identify a fitness level change. The method further includes receiving an update data associated with an update training activity, and identifying an updated training intensity utilizing the update data. In one example, the plurality of training activities are running activities and the updated training intensity is a training pace. In a further non-limiting example, the plurality of training activities are swimming or cycling activities.

In one example, an apparatus includes a processor, a user interface, an interface configured to receive a heart rate data from a heart rate monitor, and a navigation system configured to monitor a user navigation data comprising user location data and user speed data. The apparatus includes a memory storing an application comprising instructions executable by the processor, the application configured to output a plurality of prompts at the user interface during an athletic activity, the plurality of prompts configured to assist in determining an updated current training pace, wherein the application is further configured to determine an updated current training pace from a training data monitored during the athletic activity. In one example, the athletic activity is a running activity. In a further non-limiting example, the athletic activity is a cycling activity, swimming activity, or walking activity.

In one example, a fitness level monitoring method includes receiving a baseline data associated with a baseline athletic activity, the baseline data comprising a navigation data, a heart rate data, and a pace data. The method includes receiving a training data associated with a plurality of training athletic activities, and processing the training data to identify a training athletic activity from the plurality of training athletic activities usable to identify a fitness level change. The method includes identifying a user fitness level change. In one example, the athletic activity is a running activity. In a further non-limiting example, the athletic activity is a cycling activity, swimming activity, or walking activity.

In one example, a method includes receiving a training data associated with a plurality of user athletic activity, the training data comprising navigation data, heart rate data, and pace data. The method includes receiving a data associated with a current fitness level determination, and processing the data to predict an estimated race performance time. For example, the current fitness level determination comprises a training pace update activity. In one example, the method further includes identifying a need for a training pace update activity.

In one example, a fitness level monitoring method includes receiving a baseline data associated with a baseline activity, the baseline data comprising a heart rate data, and a movement data. The method includes receiving a fitness test data, and processing the baseline data and the fitness test data to identify a user fitness level change. In one example, the movement data is associated with user running. In a further non-limiting example, the movement data is associated with user walking, cycling, or swimming.

Advantageously, these methods and apparatuses allow the user to train at determined optimized training paces reflecting their current fitness level without the need to constantly perform a lactate threshold test to determine their current fitness level. Furthermore, the user need not constantly perform a race in order to estimate their current fitness level, avoiding the stress on the body of running a race and the need to interrupt their training to perform a race at peak performance. To run a race, the user must taper their training in advance of the race, and may need recovery time after the race before resuming normal training.

Simultaneously, these methods and apparatuses avoid the limitations of heart rate based training used alone. These limitations are due to the variety of factors affecting a user heart rate during running which are independent of the user fitness level. Such factors include ambient temperature (or other weather factors), stimulant intake (e.g., caffeine), the course topography and elevation profile, time of day, length of time into the run, the user stress level, whether the user is dehydrated, or even variability of the heart rate monitor. Furthermore, the user heart rate may vary due to simple day to day variations of up to 2-3 beats per minute. Furthermore, it is easier psychologically for the user to maintain a desired pace than a desired heart rate. For example, it is intrinsically easier for a user to know how to maintain a target pace of 8:00 minutes per mile than a heart rate of 165 bpm.

Furthermore, heart rate based training methods in the prior art are not specific to the user, failing to account for heart rate variations from user to user based on training data. For example, the average heart rate for a user A running at marathon pace may differ from the average heart rate for a user B running at marathon pace.

Methods and apparatuses described herein utilize heart rate data, but do so in a matter which reduces or eliminates these prior art problems by (1) only using heart rate data periodically, i.e., limiting its use, (2) personalizing it to each specific user based on actual training data, and (3) when it is used (e.g., in pace update runs), minimizing the effect of factors which affect HR independent of the user fitness level (e.g., performing the pace update run on the same course as the baseline run).

FIG. 1 illustrates a system for athletic performance monitoring being worn by a walker or runner 1 in one example. FIG. 1 shows a walking or running person 1 wearing a training device 2 around his wrist and wearing athletic shoes to which a sensor unit 4 is attached. However, the sensor unit 4 may also be incorporated in the sole of the shoe or elsewhere on or within the shoe. The sensor unit 4 may also be attached directly to the foot of the person. The person 1 is also wearing a sensor unit 6 around his torso.

Training device 2 and sensor units 4 and 6 are placed on or attached to person 1 directly or indirectly. For example, training device 2 and sensor units 4 and 6 may be attached to or on, placed within, or otherwise integrated with worn shoes, accessories, clothing, or equipment. Training device 2 and sensor units 4 and 6 may be mounted directly on runner 1 by adhesives, bands, straps, hooks, other mechanical connectors.

In some examples, the training device 2 may be attached to the user's wrist in an enclosure which is similar to a watch and combined with other functionality such as timekeeping or with other sensors such the navigation device. In further examples, the training device 2 may be attached to the user's arm using an enclosure similar to an armband and combined with other devices such as a cellular phone, an audio device and/or the navigation device.

In some examples, the sensor unit 4 may be attached to the top of a user's shoe with removable fasteners such as clips. In other examples, the sensor unit 4 may be inserted within the user's shoe, such as within a recess formed in the sole of the shoe.

In one example, the sensor unit 6 includes one or more sensors 50 (e.g., heart rate sensors or accelerometers) or other inertial sensors and may be attached to the user with a chest strap in an enclosure which may include other sensors such as a heart-rate monitor (HRM) sensor. In the example shown in FIG. 1, sensor unit 6 includes sensors 50a and 50b which are heart rate sensors mounted in parallel on both the left and right side of the runner 1 torso. Sensor unit 6 may also include tri-axial accelerometers.

In further examples, any number of sensors may be provided to sense any desired type of athletic performance information. Furthermore, as used herein, the term "sensor" may refer to one or more sensors. Sensor of varying types may be placed at the same desired location on runner 1. For example, training device 2 may include both an inertial sensor and a GPS unit. Sensor unit 6 may include both an inertial sensor and a heart rate sensor.

Training device 2 and sensor units 4 and 6 are operable to communicate wirelessly amongst themselves. In the example shown in FIG. 1, sensor unit 6 is in communication with training device 2 via a wireless link 3 and sensor unit 4 is in communication with training device 2 via a wireless link 5.

Training device 2 may also be configured to communicate with computing devices, exercise devices, navigation devices, sensors, and any other enabled devices through a communication network, such as a local area network, a wide area network, or the Internet. Such communication may occur via wired or wireless links.

In the example shown in FIG. 1, training device 2 for has been incorporated into a wrist-worn device. For example, wrist worn device may assume a watch form factor having some form of visual display and audio output. Data collected by sensor unit 4 and sensor unit 6 are transmitted to training device 2 (i.e., the wrist worn device) for processing and/or output together with data collected by training device 2. The collected sensor data is processed, stored, and/or displayed at training device 2.

In a further example, data collected by training device 2 and sensor units 4 and 6 are transmitted to an electronic device for processing, where the electronic device need not itself have a sensor. For example, the electronic device may be an MP3 or other type of digital music player, watch, handheld computing device, cellular telephone, or any other device capable of displaying information or outputting audio. The electronic device may process the received sensor data and output associated information to the user via a user interface output such as a LCD display. The electronic device may be attached to the runner's body in any manner similar to that of a sensor so that it is easily carried, moved, heard, or viewed during running. Utilizing the user interface 7, real-time feedback is provided as to the user's arm/opposite leg synchronization, arm rotation across the torso, and vertical/horizontal displacement ratio.

Figure 2:
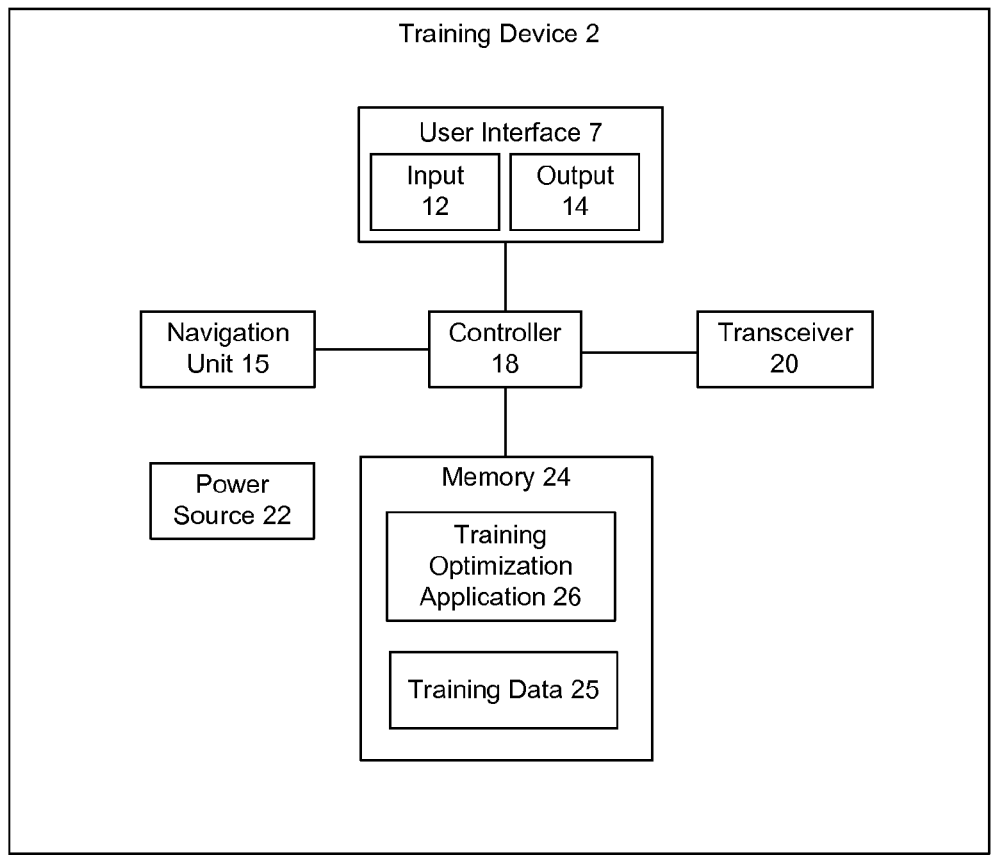
FIG. 2 illustrates a simplified block diagram of the training device shown in FIG. 1 in one example.

FIG. 2 illustrates a simplified block diagram of training device 2 shown in FIG. 1. In one example, training device 2 is a wrist worn device such as a watch. Although shown worn on the wrist, training device 2 may be worn on the user's forearm, arm, or elsewhere in further examples. In further examples, training device 2 may be a smartphone or other mobile device. The various components of training device 2 may be housed integrally or separately in any combination.

Training device 2 includes a navigation unit 15 adapted to provide geographic location information. In one example, navigation unit 15 is a GPS unit including a GPS receiver and antenna. The GPS unit is adapted to provide geographic location information for the device 2 based on signals received from orbiting satellites. In a further example, navigation unit 15 may use cellular (i.e., via a cellular transceiver operable on a cellular communications network) or other positioning signals instead of the GPS to determine geographic position and generate navigation information. Navigation unit 15 is operable to determine speed, current and previous locations, bearing and heading, and altitude of a user. Navigation unit 15 is operable to calculate position and display map, route, and location information. Map information stored in memory 24 may be retrieved and displayed on a device display along with the calculated position information.

Training device 2 includes a user interface 7. User interface 7 includes an input device 12 and an output device 14. For example, input device 12 may be one or more buttons, switches, a touch bezel, or a touch screen.

Output device 14 may include speakers for outputting audio and a visual display screen. The output device 14 may also include a vibrate element to notify users of information via mechanical vibration. The user interface 7 may also include various processing and memory devices to facilitate its functionality. The user interface 7 is operable to receive inputs from the user to control the functionality of the training device 2 and elements associated therewith.

Output device 14 enables users to receive real-time feedback concerning user motion parameters and associated information. For instance, the user interface 7 may monitor and present the current pace (instantaneous pace, average pace for the duration of the current activity, average pace during the current lap, average pace for the previous lap), distance (distance travelled during the current activity, distance traveled during the current lap, distance remaining), time (and amount of time during the current lap, amount of time during the last completed lap, stopwatch time, elapsed time), heart rate (instantaneous heart rate, average for the duration of the current running activity, average in the current lap, average during the last completed lap, percentage of heart rate reserve, percentage of maximum heart rate), or combinations thereof.

In various examples, the training device 2 is configurable to monitor estimated motion parameters and alert the user through the output device 14 when one or more estimated motion parameters either fall within or fall outside a user-defined condition such as an acceptable parameter range, threshold, or variance. For example, training device 2 may be configured to prompt the user to maintain a target pace, target pace range, target heart rate, or target heart rate range for a specific time or distance interval(s), or across the entire run. Training device 2 may offer a virtual pacer function (also referred to as a virtual partner) whereby training device 2 monitors the performance of the runner relative to a virtual pacer set to run a particular pace, and outputs feedback to the user the distance and time the user is ahead or behind of the virtual pace during the duration of the current activity. Such virtual pacer functions are known in the art. Training device 2 is configurable to monitor any parameter as described herein.

Training device 2 also includes controller 18, transceiver 20, power source 22, and memory 24. Controller 18 may include one or more signal processors. In one example, power source 22 is a battery, which may be rechargeable or not rechargeable.

Memory 24 may include any computer-readable memory or combination of computer-readable memories operable to store data for use by the controller 18. For instance, the memory may be operable to store acceleration data, motion parameter metric data, statistical data, motion parameter data, filtering data, configuration data, or any combination thereof.

The controller 18 may include various analog and digital components operable to perform the various functions discussed herein. For example, the controller 18 may include a microprocessor, a microcontroller, a programmable logic device, digital and analog logic devices.

The controller 18 additionally utilizes information acquired from sensors via wireless links using transceiver 20 to enable real-time comparison of information generated by various sensors in the system. For example, the controller 18 receives information from sensor unit 4 and sensor unit 6 to generate one or more motion parameters using such information.

Similarly, the controller 18 may couple with other sensors to acquire any type of information. For example, to acquire additional information, the controller may couple with, and/or include, gyroscopes, altimeters, compasses, and pressure sensors, and other inertial sensors, or any combination thereof, disposed at training device 2, sensor unit 4, sensor unit 6, or elsewhere.

Utilizing various signal processing algorithms, the controller 18 may analyze and compare measurements provided by sensors 40 at sensor unit 4, and sensors at 50 sensor unit 6. Controllers at each sensor unit 4 and 6 may implement similar signal processing algorithms.

Figure 3A:
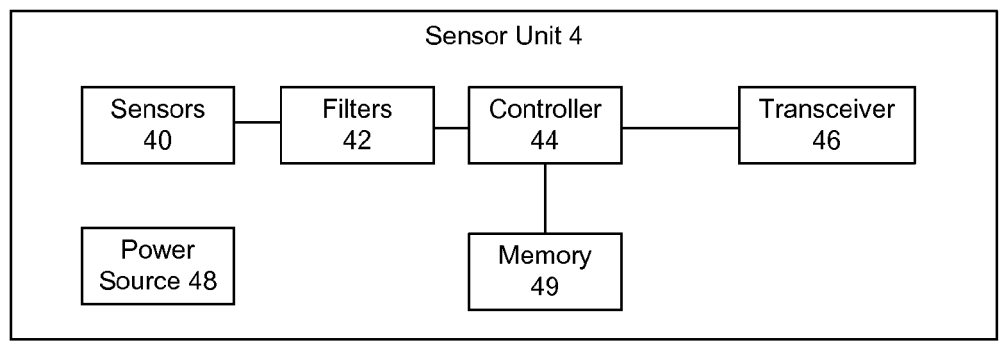
FIG. 3A illustrates a simplified block diagram of a foot mounted component of the system shown in FIG. 1.

FIG. 3A illustrates a simplified block diagram of a foot mounted component, sensor unit 4, of the system shown in FIG. 1. Sensor unit 4 includes sensors 40, filters 42, controller 44, transceiver 46, power source 48, and memory 49. Controller 44 may include one or more signal processors. In one example, power source 48 is a battery.

Sensor unit 4 includes one or more sensors 40. In one example, sensors 40 include one or more accelerometers. In a further example, sensors 40 include a gyroscope in addition to an accelerometer. In one example, the accelerometer is a tri-axial accelerometer. In one example, the one or more accelerometers are linear accelerometers.

The sensors 40, filters 42, and controller 44 may be integrated together or form discrete elements that may be associated with each other. The controller 44 is operable to analyze measurements provided by the sensors 40 to estimate parameters corresponding to one or more parameter types.

The sensors 40 are each operable to measure an acceleration and generate an acceleration measurement corresponding to the measured acceleration. The acceleration measurement may be embodied as a signal operable to be utilized by the filter 42 and/or controllers 18 and 44.

In some embodiments, one or more of the sensors 40 may be operable to output an analog signal corresponding to an acceleration measurement. For instance, each accelerometer may output an analog voltage signal that is proportional to measured accelerations.

However, the one or more sensors 40 may include any digital and analog components operable to generate a signal corresponding to a measured acceleration. Thus, in some embodiments, one or more of the sensors 40 are operable to output a digital signal representing measured accelerations. Further, in some embodiments, one or more of the sensors 40 may comprise linear accelerometers.

In some embodiments, more than one of the sensors 40 may be integrated into the same integrated circuit package to allow the single package to provide acceleration measurements along more than one axis. Sensors 40 may each include two or more accelerometers each operable to output a signal corresponding to a measured acceleration.

In some examples, sensors 40 each include two accelerometers adapted to measure accelerations in two directions separated by an angle greater than zero degrees and each provide a signal corresponding to the measured acceleration. In some examples, sensors 40 may each include at least three accelerometers adapted to measure accelerations in three directions each separated by an angle greater than zero degrees and each provide a signal corresponding to the measured acceleration. In some embodiments, the three accelerometers may be oriented in a mutually perpendicular configuration. In one example, sensors 40 are a triaxial accelerometer. However, sensors 40 may include any number of accelerometers, including a single accelerometer positioned in any configuration to provide acceleration measurements.

Transceiver 20 and transceiver 46 are configured for wireless communication using various RF protocols. For example, transceiver 20 and transceiver 46 may communicate utilizing Bluetooth, ANT, and/or any other wireless protocols.

The filter 42 is operable to couple with the one or more accelerometers and filter acceleration measurements and/or signals corresponding to acceleration measurements. The filter 42 may include analog and digital components operable to filter and/or provide other pre-processing functionality to facilitate the estimation of motion parameters by the processors at controllers 18 and 44. In various examples, the filter 42 is operable to filter signals provided by the one or more accelerometers, or signals derived therefrom, to attenuate perpendicular acceleration, to compensate for gravity, and/or to minimize aliasing. The filter 42 may include discrete components for performing each of these filtering functions or use the same components and hardware for these, and other, filtering functions.

The anti-aliasing provided by the filter 42 generally reduces or prevents aliasing caused by sampling of the signals provided by, or derived from, the one or more accelerometers. In some embodiments, the filter 42 include a relatively wide-band filter designed to attenuate signal frequencies in excess of one-half of the sampling frequency used in any subsequent analog-to-digital conversions provided by the controllers.

The filter 42 may include any analog and digital components for filtering signals and measurements, including passive and active electronic components, processors, controllers, programmable logic devices, digital signal processing elements, combinations thereof, and the like. The filter 42 may also include an analog-to-digital converter to convert analog signals provided by the one or more accelerometers to digitize signals for use by the processors at controllers 18 and 44. The filter 42 may also include conventional pre-sampling filters. In some examples, the low-pass filter 18 may be an adaptive filter operable to employ static and/or varying cut-off frequencies between about 0.5 Hz and 10 Hz.

Figure 3B:
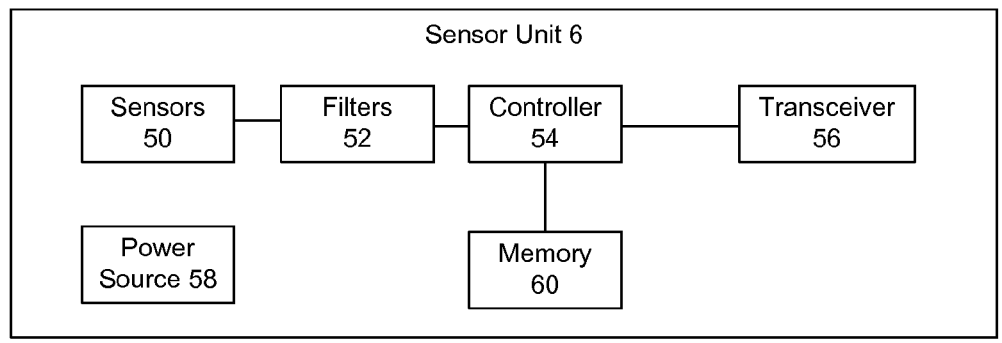
FIG. 3B illustrates a simplified block diagram of a torso mounted component of the system shown in FIG. 1.

FIG. 3B illustrates a simplified block diagram of a torso mounted component, sensor unit 6, of the system shown in FIG. 1. Sensor unit 6 includes sensors 50, filters 52, controller 54, transceiver 56, power source 58, and memory 60. Controller 54 may include one or more signal processors. In one example, power source 58 is a battery. Operation of the various components of sensor unit 6 are substantially similar to that of the similarly named components of sensor unit 4 described above with respect to FIG. 3A.

Sensor unit 6 includes one or more sensors 50. Sensors 50 include a heart rate monitor. In a further example, sensors 50 include one or more accelerometers. In one example, sensors 50 include a pair of sensors 50a and 50b which are heart rate sensors as shown in FIG. 1.

Referring again to FIG. 2, memory 24 stores various training data 25 gathered during user activity. For example memory 24 stores training data 25 including a baseline data associated with a baseline run, a training data associated with one or more training runs, a fitness test data associated with a fitness test run, and an update data associated with a training pace update run (i.e., a fitness level determination run or a fitness level update run or a training intensity update run). Memory 24 stores for example, geographical location data, total time, total distance, split data (including time, average pace, and average heart rate for each split), heart rate information, and average speed for each run.

Memory 24 also stores a training optimization application 26 configured to process the baseline data and the fitness test data to identify a user fitness level change. The training optimization application 26 is further configured to identify a need for a training pace update run. The training optimization application 26 is configured to process the update data to determine an updated current training pace. In one example, training optimization application 26 may be uploaded to device 2 as a plug-in to an existing application on device 2 performing monitoring and training functions known in the art. In a further example, training optimization application 26 is integrated with an existing application on device 2 into a single application program performing all of the functionality described herein at the time of manufacturing.

In one example, the system further includes a headset configured to receive and output audio prompts to a user.

In one example, the training optimization application 26 is configured to process the navigation data to identify a current start location of the user, search the training data to identify a training run having a same start location as the current start location, and prompt the user during the training pace update run to run a route corresponding to the training run having a same start location as the current start location, wherein the training optimization application 26 is further configured to prompt the user to maintain a target heart rate determined from the training run having a same start location as the current start location.

In one example, a baseline, current fitness level is utilized at the start of training. The baseline, current fitness level can be determined utilizing a variety of methods. For example, the runner may have a lactate threshold test performed or may run a race to determine the runner's current fitness level. The results are utilized to determine the correct pace (the current "training pace") at which to perform various workouts. Workouts typically include Long Runs, Intervals, Easy Runs, Threshold Runs, Tempo Runs, etc., each of which are performed at a different training pace in accordance with a typical training plan. In some training plans, training paces include base pace, marathon pace, lactate threshold pace, 10 k pace, 5 k pace, and 1500 m pace. Particular names for the workouts and the training paces may vary from training plan to training plan. For example, in some training programs "tempo runs" are performed at marathon pace, and "threshold runs" are performed at lactate threshold pace. Different kinds of Intervals are performed at 10 k pace, 5 k pace, or 1500 m pace, depending upon the Interval. The current training pace for each of these different paces may be calculated or determined from a lookup table using the results from a recent race or the results of the lactate threshold test. These types of lookup tables are known in the art.

For example, a lookup table is found in "Daniels' Running Formula", $2^{nd}$ Edition, by Jack Daniels. Similar lookup tables are provided in "Brain Training for Runners", by Matt Fitzgerald. The tables are generated based on determining a user's VDOT (V dot O2 max) from a recent race performance. For a given VDOT, the table provides the correct current training intensity (i.e., the current training pace) for various training types, including marathon pace, lactate threshold pace, and everyday easy runs. Other paces, including 10 k pace and 5 k pace can be determined using predicted 10 k and 5 k race times from the recent race performance.

Alternatively, running calculators are available online whereby the user enters his most recent race time (whatever the race distance), and the appropriate pace levels are calculated and provided to the user. This allows the user to enter an exact race time for the calculation of training paces as opposed to using the closest race time available in the lookup table. For example, such a calculator is available from Jack Daniels at http://runsmartproject.com/calculator/. Tables and calculators from other sources are available and known in the art, and may vary slightly in calculated paces and the specific training paces calculated. In one example, tables are generated by the manufacturer and pre-installed in the device memory at the manufacturer for use as described herein.

FIG. 4 shows a portion of an illustrative lookup table utilized to determine training paces. In one example, a complete lookup table showing a broader range of race times is stored in memory 24 for use by training optimization application 26 as described herein. In a further example, the user may manually look up their paces and manually enter them into training device 2. In yet another example, training optimization application 26 incorporates a running calculator which determines the training paces from the race result. In one example, a lookup table shown in FIG. 4 or similar is generated using a running calculator by entering race times at pre-determined intervals and generating the training paces for each race time and corresponding race time equivalents, where the results are stored in a table for use in lookup form and reverse-lookup form. For example, smaller time intervals between race times (e.g., race times with increasing increments of 5 seconds) may be used than that shown in FIG. 4 so that a more accurate approximation can be used when looking up a race time not having an exact match in the table.

FIGS. 5A and 5B illustrate excerpts of lookup tables utilized to determine training paces in a further example which may be used instead of the table found in FIG. 4. To utilize the tables in FIGS. 5A and 5B, the user enters a recent race performance time (e.g., 5 k, 10 k, half marathon, or marathon) and the training optimization application 26 identifies the user training pace level (PL) using the lookup table FIG. 5A (which is stored in memory of device 2). The training optimization application 26 then utilizes the lookup table found in FIG. 5B to determine the various current training paces.

In various examples, training optimization application 26 may use different sources, or the user himself may enter the current training paces into training optimization application 26 having looked them up himself using his desired source. As described earlier, the training paces (e.g., base pace or easy pace) for a given race time may vary slightly from source to source depending on the training philosophy or methodology. Where the runner performs a lactate threshold test to determine his lactate threshold pace, the lookup table (e.g., FIG. 4) is utilized in reverse (i.e., a reverse lookup table) to determine other training paces corresponding to the measured lactate threshold pace.

In one example, training optimization application 26 is configured to automatically identify a running activity which is a race and automatically update training paces based on the race time. In one example, training optimization application 26 identifies that an activity is a race by determining whether the heart rate profile matches a race heart rate profile indicating a maximum or near maximum effort (e.g., heart rate average above a certain level).

If the user has not previously run a race or performed a lactate threshold test, training optimization application 26 may determine the initial training paces using an alternative method. In one example, the runner is prompted to perform a "time trial" (e.g., 5 k) of a user desired difference, the results of which the training optimization application 26 treat as a race for purposes of determining the initial training paces.

In a further example, the training optimization application 26 determines a particular training pace (e.g., lactate threshold) by prompting the user to run at target heart rate estimated to correspond to that particular training pace. At the end of the run, training optimization application 26 identifies the user's average pace and sets this to be the current training pace. Other training paces can be determined using this pace and lookup tables as described herein. Alternatively, other training paces may be determined by prompting the user to run at a target heart rate range estimated to correspond to the other training paces. For example, the training optimization application 26 is configured to prompt the user to run at 74-84% of their maximal heart rate for a base pace, 79-88% of their maximal heart rate for marathon pace, 82-91% of their maximal heart rate for a lactate threshold pace. Less desirable, but also possible is for the runner to perform a generic running activity with no target and training optimization application 26 can determine the runner's current fitness level (e.g., current training paces) using the average heart rate and the pace of the run. Once these initial training paces are determined, they are used in the same manner as if they were determined from a race performance or lactate threshold test in the methods and apparatuses described herein. These initial training paces may be reset following the performance of a race or lactate threshold test, or as described herein as the user fitness level changes.

For example, a training plan may call for a "long run" workout to be performed at a "base pace". The runner's current "base pace" is dependent upon the runner's current fitness level.

In one example, a fitness level monitoring method includes receiving a baseline data associated with a baseline run, the baseline data comprising a navigation data, a heart rate data, and a pace data. A baseline run is performed by the runner for a given workout at a start of the training cycle. For example, the training plan may call for a baseline "long run" to be performed at the runner's base pace. The runner may use this "long run" as his baseline run. During the baseline run, training device 2 tracks the precise route performed by the runner, the runner heart rate (HR) during the run (received from sensor unit 6), and the runner pace. The training device 2 executes training optimization application 26. In one example, the runner is prompted to perform the run at the runner's current training pace appropriate for the type of run being performed (e.g., base pace for a long run). The current training pace for the base pace may be stored in memory at the training device and selected by the user at the start of the run, or the runner may manually enter the base pace. In one example, during the baseline run, the training device 2 continually monitors the user pace and prompts the user to either increase or decrease pace to match the current training pace. In one example, the training device 2 may track "split" data, e.g., every 0.25 mile. As part of the routing information tracked, the training device 2 may also track altitude and elevation changes of the route which is run. Also monitored may be the time of day and a date of the run, and the temperature during the run.

The runner may perform one or more baseline runs at the start of the training cycle. For example, the runner may perform a baseline run for several different types of workouts (e.g., long run, tempo run, intervals), where each workout is performed at a current particular training pace (e.g., base pace, threshold pace, marathon pace, etc.) as called for by a training plan.

The method includes receiving a training data associated with a plurality of training runs and processing the training data to identify a need for a fitness test run. For example, following the baseline run, the runner performs workouts prescribed by their training plan. If not following a training plan, the runner simply performs runs as desired.

The training device 2 may automatically and advantageously determine when it is appropriate for the runner to perform a fitness level test. The training device 2 bases the determination on analysis of the workouts performed subsequent to the baseline run. All workout data is stored in a computer readable memory which is accessible to make the determination. In one example, the determination is based on the total number of miles run since the baseline run. In one example, the determination is based on the total number of miles run above a certain heart rate since the baseline run. In a further example, the determination is based on the time elapsed from the baseline run (e.g., 1 month).

The method includes receiving a fitness test data associated with a fitness test run. In one example, the training device 2 (executing training optimization application 26) prompts the runner to perform a fitness level test (i.e., fitness level run).

To perform the fitness level test, the runner runs the same route that the baseline run was performed at. In one example, the training device 2 prompts the runner with the name of the route to be run. The name may be a name entered by the runner following the baseline run. During the fitness level run, the training device 2 may retrieve the routing information from the baseline run and use this navigation/location data to prompt the runner during the run with turn by turn directions on the precise route to follow to match the baseline run.

In one example, the training device 2 may prompt the runner to perform the fitness level run at a time of day close to the time that the baseline run was performed.

During the fitness level run, the training device 2 paces and prompts the runner to perform the fitness level run as close to the pace of the baseline run as possible. In one example, the training device 2 simply instructs the runner to perform the fitness level at the base pace if the baseline run target pace was the base pace. In a further example, the training device 2 retrieves the pacing information as a function of time during the run from the baseline run and uses this data to pace the runner during the fitness level run at the same pace that the baseline run was performed. This is particularly advantageous if the runner varied his pace during the baseline run, either due to elevation changes or other reasons. Thus, the runner can use virtually any type of run as the baseline run, and it need not be at the same pace throughout the run.

During the fitness level run, the training device 2 tracks all data (e.g., HR data, pace data, etc.) that was also previously monitored during the baseline level run.

The method includes processing the baseline data and the fitness test data to identify a user fitness level change. Following the fitness level run, the training device 2 analyzes the baseline run data and the fitness level run and determines whether the runner has improved his fitness level since the baseline run. The training device 2 may also determine that the runner has decreased his fitness level.

In one example, the training device 2 determines whether the runner has improved his fitness level by comparing heart rate data. For example, the average HR across the entire baseline run may be compared to the average HR across the entire fitness level run. If the average HR has decreased by more than a certain threshold level (e.g. 3 beats per minute (bpm)) in the fitness level run compared to the baseline run, then the training device 2 designates a fitness level improvement. All heart rate values described herein are given in bpm, even if not explicitly designated as such.

In a further example, the average HR for each split of the baseline run is compared to the same corresponding split of the fitness level run. If the average HR for a threshold number of splits of the fitness level run is less than the baseline run by more than a threshold level (e.g., 3 bpm), the training device 2 designates a fitness level improvement. In either case, the threshold level heart rate difference may be set by the manufacturer. The level may be set high enough so that variations in HR unrelated to fitness level improvement do not trigger a fitness level improvement designation. In one example, the threshold level is set high enough so that a minor improvement in fitness level does not trigger a fitness level improvement.

In one example, the user need not designate a particular run as a "fitness test run", as the training optimization application 26 may identify a running activity that the user performs in the course of his training program or exercise plan which can be used as the fitness test run. For example, the training optimization application 26 may identify one or more running activities whereby the user runs the same course at the same pace as the baseline run. The training optimization application 26 then determines a fitness level change utilizing the heart rate data of these runs.

In one example, if the training device 2 determines a fitness level improvement, the runner is prompted to perform a pace determination run (also referred to herein as a pace "update run") to determine an updated current training pace. For example, the runner may be prompted to perform the pace determination run after the runner has recovered or one week later as part of the runner's regularly scheduled training plan. In one example, the training device 2 prompts the runner with the name of the route to be run. As with the fitness level run, the pace determination run is performed on the same route as the baseline run. In a further example, the runner is prompted to perform a pace determination run based on the elapsed time since a previous pace determination run was performed.

During the pace determination run, the training device 2 paces and prompts the runner to perform the run as close to the heart rate of the baseline run as possible. The training device 2 retrieves the HR information as a function of time during the run from the baseline run and uses this data to pace the runner during the fitness level run to run at the same HR that the baseline run was performed at each point of the run. For example, the prompts may be audio prompts output at a headset or using vibrate and/or text alerts at training device 2.

During the pace determination run, the training device 2 tracks all data that was previously monitored during the baseline level run, including user speed throughout the run. In a situation where the runner's fitness level has improved, the user speed during the pace determination run will be faster than the speed of the baseline run since the run is being performed at the same heart rate. In a situation where the runner's fitness level has decreased, the user speed during the pace determination run will be slower than the speed of the baseline run since the run is being performed at the same heart rate. In one example, the data received at training device 2 during the pace determination run is processed to calculate the average pace of the user.

The average user pace during the pace determination run is updated to be the current pace at which training should be performed moving forward for the particular pace category of the baseline run and the pace determination run, (e.g., "Base pace"). Utilizing a lookup table or a pace calculator, other pace types are updated as well utilizing this average user pace during the pace determination run.

To illustrate examples of the apparatuses and methods described herein, particular examples using sample data numbers will be described below. These example are illustrative only, and do not reflect all of the examples described above.

Example 1

A runner runs a half marathon in a time of 1 hour and 45 minutes. Utilizing a lookup table as described above, this time corresponds to the following training paces (in minutes/mile): Base Pace=9:00, Marathon Pace=8:15, Half Marathon Pace=7:57, 10K pace=7:34, etc. In one example, the user enters his time of 1 hour and 45 minutes into the training device 2 and the training device 2 utilizes a lookup table of training paces based on race times stored in memory. In a further example, the runner may look up the paces manually and enter the appropriate pace prior to each running activity. These paces are the current training paces reflecting the user's current fitness level based on his race performance.

In this example, the runner is following a training plan which calls for a "Long Run" of 12 miles to be performed at "Base Pace" shortly after his race. The runner may select to use this run as his baseline run. However, the runner could also use a tempo run as his baseline run or other type of workout.

The runner performs the scheduled Long Run at his base pace of 9:00 minutes/mile. In one example, the runner designates at the training device 2 that this is a baseline run. During the run, the training device 2 receives various data associated with this baseline run, including HR data, pace data, and navigation data. The training device 2 records the start location, route, and end location. The user may be prompted to give this run a name, such as "Ocean Drive Long Run". During the run, the training device 2 may prompt the runner to maintain a pace of 9:00 minutes per mile if the runner deviates by a predetermined amount (e.g. 5 seconds) from 9:00 minute/mile pace. Split times may be output as set by the user for any desired distance. In one example, the training optimization application 26 configures a workout (e.g., Long Run at Base Pace) which the user executes, whereby the training optimization application 26 sets the virtual pacer to 9:00 minutes per mile, or configures alerts to be output if the user pace deviates from a pace of 9:00 minutes per mile by more than a threshold amount (e.g., plus or minus 10 seconds per mile).

Following completion of the Long Run, the runner may also perform other types of workouts and designate these workouts as baseline runs as well. The baseline runs are stored in memory at the training device 2 and categorized by workout. All data referenced herein may also be transferred from training device 2 to a computing device executing an application capable of performing the functions performed by the training optimization application on training device 2.

Following the baseline Long Run, the user performs a variety of workouts in accordance with his training plan. Data from all workouts is stored at training device 2. The training device 2 tracks all collected data and determines when it is appropriate to perform a fitness level test. For example, training device 2 identifies a training run usable to identify a fitness level change. For example, a fitness level test may be performed after the user has run 200 miles since the baseline run.

After the runner runs over 200 miles, the runner is prompted to perform a fitness level test. The runner may select the type of workout to perform the fitness level test based on the baseline runs stored in memory. For example, the runner selects to perform the "Ocean Drive Long Run" Long Run to perform his fitness level test.

To perform the fitness level test, the runner runs the same exact course stored as "Ocean Drive Long Run" that was run during the baseline run. Or the runner may run any other course for which a baseline run was performed. The training device 2 retrieves navigation information from the baseline run and prompts the runner accordingly with turn by turn directions on how to run the same exact route. The runner is to perform the fitness test by running at the same pace as the baseline run was run, in this case, 9:00 minutes per mile. The training device 2 retrieves pace data from the stored baseline run and prompts the runner during the fitness run accordingly to increase or decrease his pace to match the baseline run.

Following the completion of the fitness level run, training device 2 (or other computing device if data is transferred from training device 2 and processed at the computing device) processes the data from the baseline run and the fitness run to identify a fitness level change. For example, if the runner has an average heart rate of 164 during the baseline run and an average heart rate of 158 during the fitness level run, the system outputs an indication that the runner's fitness level has improved. In one example, training optimization application 26 identifies that this run is usable to identify a user fitness level change. Other metrics besides HR may be utilized to determine improved fitness.

Since the runner has improved his fitness, the runner decides to perform a pace update run. This run will allow the runner to update his current training paces. The runner is prompted to perform a pace determination run. The pace determination run is performed by running the same exact course stored as "Ocean Drive Long Run" that was run during the baseline run. Alternatively, another baseline run may be selected (e.g., for a marathon pace tempo run or a lactate threshold pace threshold run).

During the pace update run, the training device 2 retrieves navigation information from the baseline run and prompts the runner accordingly with turn by turn directions on how to run the same exact route. The runner is to perform the pace update run by running at as close to the same HR as the baseline run was run, in this case 164 beats per minute. Thus, this target heart rate of 164 is correlated to the user's base pace for a long run. This target heart rate of 164 is associated with the heart rate data from the baseline run. The training device 2 retrieves HR data from the stored baseline run and prompts the runner during the pace update run accordingly to increase or decrease his HR (i.e., by increasing or decreasing pace) to match the baseline run.

During the Pace Update Run, the goal of the user is to run at a predetermined target heart rate rather than a predetermined pace. However, in one example, the Virtual Pacer function is also utilized to guide the user to run at the predetermined target heart rate. During the run, the Virtual Pacer pace is adjustably set by training optimization application 26 as training optimization application 26 estimates the pace to achieve the predetermined target heart rate by processing received heart rate data and pace data during performance of the pace update run. Fine adjustments may be made to this estimated pace as the pace update run progresses, where the estimated pace is increased if the monitored heart rate is too low and the pace is decreased if the monitored heart rate is too high. This example is advantageous as the user may find it easier to maintain a target pace than a target heart rate. Use of the virtual pacer function allows the user to easily run (i.e., average) at the estimated pace by indicating how much/long the user needs to speed up or slow down to reach the desired average estimated pace. In a further example, the user may be prompted to stay within an estimated pace range.

Following the completion of the pace update run, the system processes the pace update run data to determine the average pace of the run. For example, the average pace during the pace update run is 8:50 minutes/mile. Since the runner's fitness level improved, he was able to run the same course at the same HR at a faster pace. The runner is informed that 8:50 minutes per mile is the new "Base Pace" in his workouts moving forward. The base pace of 9:00 is replaced with 8:50 minutes/mile at the training device 2 as the user's current base pace stored in memory. Other training paces are correspondingly updated and stored in memory as described herein. In one example, whenever training optimization application 26 is automatically configuring a workout for the user, where the workout calls for the runner to run at base pace (e.g., a long run at base pace), the training optimization application 26 automatically sets the virtual pacer to the user's current base pace (e.g., 8:50 minutes/mile) stored in memory and/or configures alerts to be output if the user deviates from this base pace. Or the next time the runner enters the desired base pace, he enters 8:50.

Thus, if the training plan calls for a long run at base pace, the runner performs the run at 8:50 minutes/mile. A lookup table as described previously can be utilized to determine the corresponding updated current training paces for 1500 m, 5 k, 10 k, threshold, half marathon, marathon, or other paces corresponding to a current base pace of 8:50.

Alternatively, if the training device 2 determines a fitness level improvement, the runner is prompted that his fitness level has improved and that the runner should run a race or have a lactate threshold test to determine a current fitness level so they can determine their new training paces.

Example 2

To illustrate one example of the apparatuses and methods described herein, a particular example using sample data numbers will be described. A runner runs a half marathon in a time of 1 hour and 45 minutes. Utilizing a lookup table, this time corresponds to the following training paces (in minutes/mile): Base Pace=9:00, Marathon Pace=8:15, Half Marathon Pace=7:57, 10K pace=7:34, etc. In one example, the user enters his time of 1 hour and 45 minutes and the training device utilizes a lookup table of training paces based on race times stored in memory. In a further example, the runner may look up the paces manually and enter the appropriate pace prior to each running activity. These paces are the current training paces reflecting the user's current fitness level based on his race performance.

The runner performs various workouts on his training plan utilizing these current training paces. Data from all workouts is stored at training device 2. Each workout is stored by a file name, either automatically generated by training device 2 or named by the runner. Each workout is also dated. The training device 2 tracks all collected data and determines when it is appropriate to perform a pace update run. For example, a pace update run may be performed after the user has run 225 miles since a pace update run was previously performed. This figure is of course arbitrary and may be set by the manufacturer or user. In a further example, a pace update run may be performed after a certain time has elapsed since the previous pace update was previously performed, e.g., 6 weeks.

To perform a pace update run, the runner is presented with workouts stored in memory from which he can select to use as a baseline. In this example, the workouts are workouts performed between 175 and 225 miles ago. Or, the user can be presented with the name of the previous pace update run, which the user may select. In this example, the runner is currently at the start location of his "Ocean Drive Long Run". The training device 2 identifies the runner's current position, and processes the stored workout data to identify workouts having a same start location and presents them to the runner for selection. In this example, the runner selects an "Ocean Drive Long Run" performed 6 weeks ago, where the runner has run 200 miles since performing this run. In other words, the runner has run 200 miles since this workout, satisfying the criteria that the selected workout to be used as a baseline be between 175 and 225 miles ago.

The runner performs a pace update by running the same course as the "Ocean Drive Long Run" performed 6 weeks ago. During the pace update run, the training device 2 retrieves navigation information from the previous running activity (e.g., the Ocean Drive Long Run 6 weeks ago) and prompts the runner accordingly with turn by turn directions on how to run the same exact route. The runner is to perform the pace update run by running at as close to the same HR as the previous running activity (e.g., the Ocean Drive Long Run 6 weeks ago) which is serving as the baseline run. The training device 2 retrieves HR data from the previous running activity and prompts the runner during the pace update run accordingly to increase or decrease his HR (i.e., pace) to match the previous running activity.

Following the completion of the pace update run, the system processes the pace update run data to determine the average pace of the run. For example, the average pace during the pace update run is 8:50 minutes/mile. Since the runner's fitness level improved, he was able to run the same course at the same HR at a faster pace. The runner is informed that 8:50 minutes per mile is the new "Base Pace" in his workouts moving forward. The base pace of 9:00 is replaced with 8:50 at the training device 2.

Thus, if the training plan calls for a long run at base pace, the runner performs the run at 8:50 minutes/mile. A lookup table can be utilized to determine the corresponding updated current training paces for 1500 m, 5 k, 10 k, threshold, half marathon, marathon, or other paces corresponding to a current base pace of 8:50.

Example 3

To illustrate one example of the apparatuses and methods described herein, a particular example using sample data will be described.

A runner, due to injury, has taken time off (i.e., a layoff) from running Upon resuming running, the runner may go out for a casual run with no particular pace, heart rate, or distance in mind. Data from this casual run is stored at training device 2. For example, the following data may be gathered and stored at training device 2 for this casual run:

Distance: 5.6 miles
Time: 48 minutes
Pace: 8:36 minutes/mile
Average Heart Rate: 176

Training device 2 utilizes training optimization application 26 to process this casual run data together with previously stored training data in memory 24 to identify that the user fitness level has changed. This may be performed automatically with no need for command by the user.

Training optimization application 26 may process previous training data to locate a recent running activity prior to the runner layoff to compare to the casual run. In one example, a "long run" workout type is used having the following data:

Distance: 14 miles
Time: 1:50:06 minutes
Pace: 7:52 minutes/mile
Average Heart Rate: 167

Training optimization application 26 identifies a decrease in user fitness level by identifying that the user heart rate has increased for the casual run for a pace that is slower than the compared "long run".

In a further example, alternatively a "tempo run" workout type performed prior to the layoff may be used having the following data:

Distance: 7.4 miles
Time: 55:05 minutes
Pace: 7:26 minutes/mile
Average Heart Rate: 173

Again, training optimization application 26 identifies a decrease in user fitness level by identifying that the user heart rate has increased for the casual run for a pace that is slower than the compared "tempo run". In one example, the user may command TA 26 to determine whether the user fitness level has changed. In a further example, TA 26 automatically processes received data to determine whether the user fitness level has changed.

In this manner, this casual run having no particular target metrics (e.g., pace, heart rate, or distance) can be used as a fitness test run to identify a user fitness level change by comparing the casual run data to training data representing the user's fitness level prior to the layoff. This methodology may be used where the user does not take a complete layoff where the runner stops running completely, but significantly decreases his running.

In one example, training optimization application 26 prompts the user to perform a pace update run following this determination of a fitness level decrease. Or, the user may simply perform a pace update run at any time if the user believes his fitness level has changed.

To perform the pace update run, the user travels to the location at which he wishes to perform the pace update run. Based on the present user start location (i.e., via GPS determination), training optimization application 26 processes previous stored training data to configure a pace update run for the user to perform. In a further example, configured pace update runs are identified by location and stored for retrieval for use at a later time. The user travels to a desired location and selects the appropriate pace update run stored in memory.

In one example, a stored baseline run for a given workout type performed at the present user start location is processed to configure the parameters of the pace update run. In one example, the "baseline run" is designated as such by the user at the time it was performed. In a further example, training optimization application 26 may determine that a run is a baseline run because it was performed after a previous pace update run where new training paces have been determined and set by training optimization application 26. In a further example, training optimization application 26 may identify that a particular running activity is appropriate to use as a baseline run.

Training optimization application 26 configures the pace update run utilizing the heart rate data for the baseline run, where the pace update run is configured to prompt the user to run as close to the heart rate of the baseline run as possible. To achieve this, training optimization application 26 examines the heart rate data as a function of time or distance during the baseline run. The pace update run may be configured to be the same length of time or the same distance as the baseline run. For example, the baseline run heart rate run data utilized is illustrated in FIG. 6. FIG. 7 illustrates configuration of a pace update run utilizing the baseline run data shown in FIG. 6.

During the pace update run, the runner is prompted by training device 2 to stay within the programmed heart rate range during each interval/split. The heart rate range for each interval is determined by the baseline run heart rate for the corresponding interval. In this example, for split/interval 1 the user average heart rate was 161 and the maximum instantaneous heart rate was 174. The pace update run heart rate range for the first interval is configured to have a median of 161 and maximum of 174, resulting in the target instantaneous heart range of 148 to 174 bpm. This range will advantageously assist the runner in achieving an average heart rate of 161 for the first interval, while avoiding unnecessary alerts that the user is running at an incorrect heart rate as his heart rate varies slightly. The user is prompted to increase or decrease his heart rate only when it falls outside the target range of each interval. Although this example baseline run is shown to only have seven intervals, with each interval being one mile, in further examples, the intervals may be smaller or larger. For example, each interval may be 0.50 miles, 0.25 miles, or 0.10 miles. In a further example, time based intervals may be utilized, such as 1 minute, 2 minutes, 5 minutes, etc. The heart rate date monitoring during the baseline run is continuous, thus any desired interval can be calculated and utilized. A smaller distance or time interval may allow the runner to more closely achieve the same heart rate during the pace update run as that in the baseline run, thereby maximizing the accuracy of the pace update run. Recall, that the baseline run was performed at a target pace representing the user's current fitness level. Advantageously, such a configuration accounts for variations in the user heart rate (1) which occur naturally whereby the heart rate gradually increases from the start of the run until it reaches an approximate steady state, for a same pace, (2) variations which occur resulting from elevation changes on the course, and (3) variations which occur due to slight deviations from the target pace during the baseline run, which may or may not be due to elevation changes. By configuring the pace update run to be performed on the same course and at the same heart rate as the baseline run, training optimization application 26 is able to increase the accuracy of the pace update run. In one example, the training optimization application 26 prompts the user with turn by turn directions to ensure that the runner runs precisely the same course (i.e., same route from the start location) during the pace update run as that of the baseline run.

In a further example, training optimization application 26 configures the pace update run utilizing the metric "average heart rate data for the duration of the current running activity"

gathered during the baseline run" in addition to or in alternative to utilizing instantaneous heart rate values. Training optimization application 26 configures the pace update run so that the target heart rate (as a function of time or distance) matches the "average heart rate data for the duration of the current running activity" profile of the baseline run. Because this metric is less susceptible to instantaneous variations since it is the average user HR for the duration of the current running activity, a more precise target HR value can be set, particularly after the initial start of the run as more data becomes available as the run progresses. In one example, the user is alerted to vary his heart rate only if this average heart rate value deviates by more than 1 bpm from the baseline run value.

In one example, a previously configured pace update run for the current start location is used. The previously configured pace update run may be stored in memory 24 as a "Pace Update Run", and may further be identified by course location and workout type, such as "Pace Update Run—Location A, Tempo Run at Marathon Pace". For example, "Location A" may be Lake Merced in San Francisco, Calif.

In one example, training optimization application 26 processes stored training data other than a user identified baseline run to configure the parameters of the pace update run. For example, training optimization application 26 may utilize another running activity as the baseline run instead of a user designated baseline run (e.g., the user designates the first run at a new updated training pace as a baseline run). For example, training optimization application 26 may process training data for several running activities performed by the user to identify the specific running activity whose heart rate data is used to configure the pace update run. Training optimization application 26 identifies user running activity performed on the same course (e.g., same route and distance from a same start location) at a same target pace (recognizing that in practice, the user may not run at exactly the same pace as the target pace and may vary by a few seconds) close in time to the baseline run. Where the running activities are performed closely in time (e.g., within the same month, two months, or quarter, which may be varied from user to user based on actual data) to the baseline run, it can be approximated that the user had the same fitness level for all the runs. In this example, the user may calculate an average heart rate for the identified activities. For example, training optimization application 26 identifies the running activity shown in FIG. 8 as satisfying the desired criteria.

In this illustrative example the average user heart rate (HR) is 172 bpm across the identified runs (marathon pace tempo runs at the course location "Lake Merced"). In one example, tempo runs varying slightly in time and distance may be used. Training optimization application 26 selects the running activity performed on 7/12 as the baseline run to configure the pace update run, as this run is a good representative to use since the average HR during this run was 172. Where an exact match is not available, a closest available may be used. Alternatively, the pace update run can be configured utilizing a compilation of data from more than one run to achieve an average heart rate of 172. In this manner, the training optimization application 26 increases the accuracy of the pace update run by ensuring the activity used as the baseline run is not an outlier with respect to user heart rate (e.g., caused by any of the factors which cause variation in user HR on a given day described herein). In this manner, training optimization application 26 correlates a target heart rate (e.g., 172 bpm) to a marathon pace tempo run. In one example, the correlation is course location specific (i.e., route specific). For example, the target heart rate may be 170 bpm for a course having a different elevation profile. Using the same process, training optimization application 26 correlates a target heart rate to other types of workouts. For example, training optimization application 26 may correlate a target heart rate (e.g., 161 bpm) to a base pace long run, or a target heart rate (e.g., 176 bpm) to a lactate threshold pace threshold run. In one example, training optimization application 26 performs the correlation using a single baseline run performed at the relevant pace (e.g., base pace, lactate threshold pace, etc.). In one example, the correlated heart rates to pace types are updated periodically to account for any changes in the correlation due to changes in user fitness level.

To configure the pace update run, the training optimization application 26 processes data associated with the 7/12 run. In particular, training optimization application 26 configures the pace update run so that the user will run the pace update run at a heart rate profile matching the 7/12 run at each stage of the run (e.g., each interval, including a beginning, middle and end), as well as having a total average HR across the entire run which matches the total average HR across the entire 7/12 run. This may be performed as described previously. For example, the data for the 7/12 run may be as set forth in FIG. 6, with the pace update run configured as shown in FIG. 7.

In one example, training optimization application 26 divides the 7/12 run (i.e., the baseline run) into time or distance intervals, and determines the average HR during that interval (e.g., from mile 0 to 0.25 of the run). Training optimization application 26 configures the device 2 so that the user is prompted during the pace update run from mile 0 to 0.25 to run at a HR which will match the 7/12 run. In one implementation, the user is prompted (e.g., by outputs at the device 2 user interface) to stay within a HR range determined by the average HR during that interval, where the user is alerted that his or her HR is too low or too high as necessary. For example, the target HR range for the pace update run interval is set to have a median of the average HR for the corresponding interval of the baseline run, and a maximum HR corresponding to the maximum HR for the corresponding interval of the baseline run. Training optimization application 26 utilizes a range because it will be difficult for the user to maintain their instantaneous heart rate at an exact target, and it is undesirable to constantly alert the user when minor variations from the target occur.

In one example, the training optimization application 26 further increases the accuracy of the pace update run by processing data receiving during the pace update run to determine when the user average heart rate while performing the run reaches the target average heart rate across the entire run. In the example of the 7/12 run, training optimization application 26 determines the point in the pace update run at which the average HR reaches 172 bpm. For example, this may not occur until halfway through the pace update run because the user HR at the beginning of the run starts at rest and gradually rises until it reaches a steady state. As such, the average heart rate for the duration of the current activity metric does not become of use until this point in the pace update run. Once this target average HR is reached, the training optimization application 26 prompts the user during the pace update run to increase or decrease their average HR (i.e., increase or decrease their speed) when the average HR across the entire run (i.e., for the duration of the current activity) deviates from the target HR (e.g., 172 bpm). Because these prompts are based on the average HR of the pace update run for the duration of the current running activity (and not the instantaneous heart rate), and this average HR is less susceptible to minor variations in pace or effort, training optimization application 26 can prompt the user to maintain the exact target HR (e.g., 172 bpm) rather than utilizing a heart rate range. Advantageously, this will ensure that the average HR across the entire pace update run matches the baseline run.

Configuration of the pace update run may be done at the time the user is going to perform the pace update run, in advance, or the configuration of a previous pace update run may be used as previously described. In one example, configuration is performed on device 2. In one example, configuration is performed on a device remote to device 2.

In one example, a pace update run is configured for multiple workout types. For example, a different pace update run is configured for workouts performed at marathon pace, lactate threshold pace, base pace, 10 k pace, and half marathon pace. Thus, the user can perform a pace update run for any pace type. In one example, each pace update run is tied to a particular course location to account for course variations (e.g., different elevation profiles). For example, 2 different "marathon pace" pace update runs may be configured, one for Location A and one for Location B. Training optimization application 26 may automatically display to the user to select or select the appropriate pace update run for the user to perform by determining the user's start location as either Location A or Location B. In one example, these pace update runs are configured in advance and may be reused as the runner's fitness changes. Periodically, the pace update runs may be re-configured when a new baseline run becomes available. The user may view the list of available pace update runs previously configured and select as desired.

Performing the Pace Update Run

To update his current training paces, the user performs a pace update run configured as described above, following the prompts output by training optimization application 26 at the user interface device 2. Following completion of the pace update run, the training optimization application 26 determines if the pace update run was successful by determining whether the user satisfied the configured parameters of the pace update run to within a configurable tolerance. For example, training optimization application 26 examines whether the average HR of the run was at the target heart rate. If yes, training optimization application 26 notifies the user at device 2 that the pace update run was successful, determines the updated current training pace associated with the pace update run, and informs the user of his new updated current training paces. For example, if the 7/12 run was a tempo run performed at "marathon pace", and if the user average pace during a pace update run performed on Dec. 1, 2012 was 8:20 minutes/mile, the user's updated "marathon pace" current training pace is 8:20 minutes/mile moving forward.

Determining Updated Current Training Paces

Training optimization application 26 then calculates an updated current training pace for other training paces in addition the updated current training pace corresponding to the training pace associated with the pace update run and stores these updated values in memory for configuring workouts. In one example, the updated paces are displayed to the user on a device display. For example, based on a "marathon pace" equal to 8:20 minutes/mile, training optimization application 26 calculates an updated lactate threshold pace, base pace, 10 k pace, etc. In one example, training optimization application 26 utilizes a lookup table to identify a marathon race time for which a marathon pace equal to 8:20 minutes/mile corresponds to a marathon time of between 3:36:24 and 3:40:39. In this manner, the pace update run can be utilized by training optimization application 26 to predict the user's marathon race time (or any other race time). The current user lactate threshold pace corresponding to a marathon pace equal to 8:20 minutes per mile is between 7:43 and 7:51 minutes per mile, the user's 10 k pace is between 7:34 and 7:42 (determined from the 10 k race time), and the current easy (e.g., base or maintenance) pace is approximately 8:36 to 9:15. Since an updated lactate threshold pace is determined, the need for an actual lactate threshold test at a laboratory is thereby unnecessary to replace an outdated test value. These times are based on the sample lookup table provided in FIG. 4. Using a more complete table or calculator, a more precise value may be obtained.

Using tables described earlier and shown in FIGS. 5A and 5B, a marathon pace equal to 8:20 approximately corresponds to a PL=37 and a predicted half-marathon time of approximately 1 hour and 44 minutes. For further accuracy, the lookup table can be provided with as much detail as necessary so that approximations are minimized. For a PL=37 and half-marathon time of 1 hour and 44 minutes, the training optimization application 26 determines the user's current training paces as follows: Base=8:47, 10 k=7:34, 5 k=7:18.

Updated Training Pace Confirmation Run

In one example, training optimization application 26 confirms the determined updated current training pace. If confirmation fails, the user may be prompted to repeat the pace update run. To confirm a determined updated current training pace, training optimization application 26 identifies whether the user average HR during a subsequent running activity performed at the updated current training pace matches the target heart rate correlated to the performed workout type. In one example, to increase accuracy, a known course is utilized. For example, the user performs the same workout as the pace update run (e.g., Location A, tempo run at marathon pace), but at the updated current "marathon pace" training pace of 8:20. If the user's heart rate profile during the workout matches the heart rate profile of the baseline run (i.e., for this "tempo run at marathon pace" workout type at Location A), then the updated current training pace is confirmed. For example, if the user on Dec. 9, 2012 runs the same course as the Dec. 1, 2012 pace update run at 8:20 pace and the average user heart rate is 172, then the updated current training paces are confirmed. In one example, the Dec. 9, 2012 run is the same distance as the Dec. 1, 2012 run. In one example, the Dec. 9, 2012 run is the same total time as the Dec. 1, 2012 run. To account for variations in HR independent of user fitness level, the training optimization application 26 may confirm the updated current training paces if the average heart rate falls within a threshold range, such as between 170-174 bpm. Where a different Location has a similar elevation profile as Location A, this different location may also be used as the confirmation run if a substantially similar tempo run at marathon pace is performed (i.e., similar in time or distance).

In a further example, the training pace confirmation run is performed on a different course and/or using a different workout type than the pace update run. For example, the user on Dec. 12, 2012 may perform the workout "Location B, long run at base pace" using an updated current base pace of 8:47. If the user's heart rate profile during the workout matches the heart rate profile of the baseline run (i.e., for this "long run at base pace" workout type at Location B), then the updated current training pace is confirmed. For example, previous training data may indicate that the user during a baseline run had an average HR of 161 for a "long run at base pace" workout type at Location B. If the user on Dec. 12, 2012 runs the same course as the previous baseline run at 8:47 pace and the average user heart rate is 161, then the updated current training paces are confirmed. To account for variations in HR independent of user fitness level, the training optimization application 26 may confirm the updated current training paces if the average heart rate falls within a threshold range, such as between 159-163 bpm.

In one example, TA 26 prompts the user to perform a workout which may be used as the training pace confirmation run. This workout may be configured by TA 26 as required. In a further example, TA 26 processes received training data to automatically identify whether a running activity may be used a training pace confirmation run. In one example, TA 26 outputs a notification to the user via a device interface whether the updated pace is confirmed or not confirmed.

Ongoing Training

Once the current training paces are determined, the user trains by performing various workout types at the appropriate current training pace. For example, the user may follow a training plan. These workouts may be automatically retrieved and automatically configured or manually configured (e.g., automatically or manually configured with respect to one or more of time, distance, intervals, target pace, virtual pacer setting, alerts) and stored in memory so that the user is prompted during execution of the workout to maintain the correct current training pace. In one example, training optimization application 26 receives and processes training data associated with these workouts to automatically identify a user fitness level change. Once a fitness level change is identified, training optimization application 26 prompts the user that a pace update run is necessary.

In one example, training optimization application 26 identifies workouts which are repeated and identifies heart rate trends. For example, the repeated workout may be the workout performed by the user as a baseline run. For example, the user may periodically perform the marathon pace tempo run at Location A at the marathon pace of 8:20 with the results shown in FIG. 9. FIG. 9 illustrates stored user running activity used to identify a fitness level change in one example.

It should be noted that the exact distance of the tempo run need not exactly match from run to run, as the average heart rate for the tempo run will not vary based on minor distance variations. In one example, training optimization application 26 may processes this data to identify a fitness level change by calculating a moving average of the user average HR of recent runs. In one example, training optimization application 26 may processes this data to identify a fitness level change by averaging the user average HR of the most recent 3 runs and identifying whether this value has increased (i.e., the user fitness level has decreased) or decreased (i.e., the user fitness level has improved) by more than 3 bpm from the average heart rate of the baseline run (172 in this example. In this case, the average of the previous 3 runs is 166 bmp, easily satisfying this criteria since it is 6 bpm less than 172.

In one example, training optimization application 26 may processes this data to identify a fitness level change by determining whether there is downward or upward trend in the last 3 runs. In the present example, there is a downward trend from 173 to 165 to 160.

In one example, training optimization application 26 may utilize data from different workout types performed at different training paces to identify a fitness level change. For example, the training optimization application 26 may utilize the most recent 2 marathon pace tempo runs and the most recent 2 base pace long runs to see whether there is a decrease in average HR for each respective workout type.

In a further example, for a given work workout type, workouts having similar profiles may be utilized to identify a fitness level change, and they need not be all performed on the same course. For example, an activity performed having a distance performed at a similar pace on a course having a similar elevation profile may be utilized. The stored user training data may be sorted based on duration of the run, course topography and elevation profile, temperature, time of day, and date.

Pace Update Run

In this example, the user chooses to perform the previously configured and used pace update run on Dec. 1, 2012 described above (Marathon Pace Tempo Run at Location A) as his pace update run on Jan. 8, 2013. In further example, as described above, other baseline runs may be used. In one example, TA 26 displays to the user available pace update runs that the user can select to perform. For example, if the user average pace during this pace update run performed on Jan. 8, 2013 is 7:54 minutes/mile (and the average HR across the entire run was the configured target HR=172), the user's updated "marathon pace" current training pace is updated to be 7:54 minutes/mile moving forward instead of 8:20.

In one example, the pace update run is further configured by setting the device 2 virtual pacer application function to an estimate of what the user's predicted fitness level is. The estimate may be based on the degree to which the user's fitness level is estimated to have improved or decreased. In the present example, where the average of the 3 previous marathon pace tempo runs is 6 bpm, the improvement in fitness level is deemed high. As a rough estimate, the VP is set at a pace of 8:00 minutes/mile. Training optimization application 26 may utilize previous training data to correlate the change in average HR (e.g., 6 bpm) to a change in pace (e.g., 15 seconds per mile).

Advantageously, this provides the user with an initial pace to begin the pace update run, which is easier for the runner to achieve than providing the user with a target heart rate alone, and assists the runner in achieving the target heart rate. Here, although the ultimate updated pace is 7:54, the initial 8:00 provides a useful estimate for the initial part of the run (e.g., the half mile or first mile), which allows the user to know approximately what pace to begin the run at. Thus, the training optimization application 26 may provide the user with prompts during the pace update run including (1) an initial estimate at the start of the run what pace the runner should use during the initial stage of the run, (2) a target heart rate range for each successive interval, and (3) an average heart rate for the duration of the run (e.g., once this average heart rate for the duration of the run reaches the target heart rate.)

Determining Updated Current Training Paces

Using the techniques described above, training optimization application 26 estimates the user's predicted marathon time is approximately 3:28:23 for a current marathon pace of 7:54.

Training optimization application 26 estimates/calculates the user's current training paces using the current marathon pace of 7:54 to be as follows: Base/Easy Pace=8:20-8:50, Threshold Pace=7:26, Interval Pace=6:48. Where a range is provided, TA 26 may arbitrarily select a pace within that range. As described previously, these values may vary slightly depending on the source of the running calculator or table. In one example, combine sources where one source provides paces not provided by another.

Updated Training Pace Confirmation Run

Using the techniques described above, training optimization application 26 confirms the determined updated current training pace. For example, on Jan. 10, 2013, the user performs Marathon Pace Tempo Run at Location A at the update current marathon pace of 7:54, and the average user heart rate is 173 for the run. As a result, the pace update results are confirmed.

For example, on Jan. 13, 2013, the user performs the workout "Location B, long run at base pace" using an updated current base pace of 8:28. At the end of the run, it is determined that the average user heart rate for this run was 160 bpm, which is within tolerance range of 161 (see above). As a result, the pace update run results are confirmed. In one example, more than one confirmation run must be performed in order for the pace update run results are confirmed.

For example, on Jan. 15, 2013, the user performs the workout "Location A, threshold run at lactate threshold pace (i.e., threshold pace)" using an updated current threshold pace of 7:29. At the end of the run, it is determined that the average user heart rate for this run was 178 bpm. Training optimization application 26 has previously processed user heart rate data during a baseline run for the workout "Location A, threshold run at lactate threshold pace (i.e., threshold pace)" to be 176, with a tolerance of plus or minus 2 bpm. As a result, the pace update run results are confirmed. In one example, more than one confirmation run must be performed in order for the pace update run results are confirmed. Advantageously, any subsequent workout for which baseline data is available can be used to confirm the pace update run.

In one example, workouts are configured automatically by the training optimization application 26. For example, a workout may be retrieved from a training plan from a calendar and configured based on the user's current training paces. For example, training optimization application 26 may automatically set the virtual pacer to the current training pace for the workout type to be performed. The training optimization application 26 may also configure the device 2 to output alerts where the user pace (either instantaneous or average for the duration of the run) falls outside a range determined by the user's current training pace or user heart rate (either instantaneous or average for the duration of the run) falls outside a desired range. In a further example, the training optimization application 26 may implement a target heart range in conjunction with the target current training pace. For example, the training optimization application 26 may identify a maximum user heart rate (maximum instantaneous heart rate or average heart for the duration of the current activity) which is allowed during the run, above which the training optimization application 26 will output an alert to the user to slow down. In one example, training optimization application 26 identifies the maximum allowable heart rate by processing previous training data of the user for the workout type being performed to identify the upper end. For example, training optimization application 26 looks at the maximum heart rate of runs performed for that workout type at a same training pace. The maximum allowable heart rate is correlated to the workout type (e.g., marathon pace tempo run, lactate threshold run, base pace long run, etc.). For example, in one example described herein, the maximum allowable heart rate may be set to 169 bpm for a base pace long run, where the target heart rate was 161 bpm for a base pace long run. In one example, the maximum allowable heart rate is also correlated to a specific course location. In one example, the user manually sets the virtual pacer to the current training pace for the workout type (e.g., marathon pace tempo run) the user is performing, and manually sets the maximum allowable HR.

Use of simultaneous pace based targets and heart rate based targets is particularly advantageous when employed during the pace update confirmation run, as there is the possibility that the updated pace is too fast, in which case the user heart rate may fall above the desired target heart rate range. Use of simultaneous pace based targets and heart rate based targets is also particularly advantageous to prompt the user to slow down if the user heart rate is too high as a result of overtraining or conditions are abnormally warm. Where the user heart rate consistently exceeds the maximum allowable heart rate for a current training pace known to be accurate, this may be a strong indicator the user is overtraining. For a threshold run, this will advantageously prevent the runner from exceeding his or her lactate threshold pace, thereby optimizing their training at threshold pace to achieve the goal of lowering their threshold pace. In one example, where training optimization application 26 determines that the current pace setting of the virtual pacer is too fast, training optimization application 26 may increase the virtual pacer pace to a pace slow enough to decrease the user heart rate below the maximum allowable level. This will allow the user to easily adjust their speed accordingly based on the virtual pacer so that the user heart rate does not exceed the maximum allowable level.

In various embodiments, the techniques of FIGS. 10-17 discussed below may be implemented as sequences of instructions executed by one or more electronic systems. In one example, the instructions may be stored by the device 2 or the instructions may be received by the device 2 (e.g., via a network connection). In one example, a training optimization application 26 executed at device 2 includes these instructions.

Figure 10:
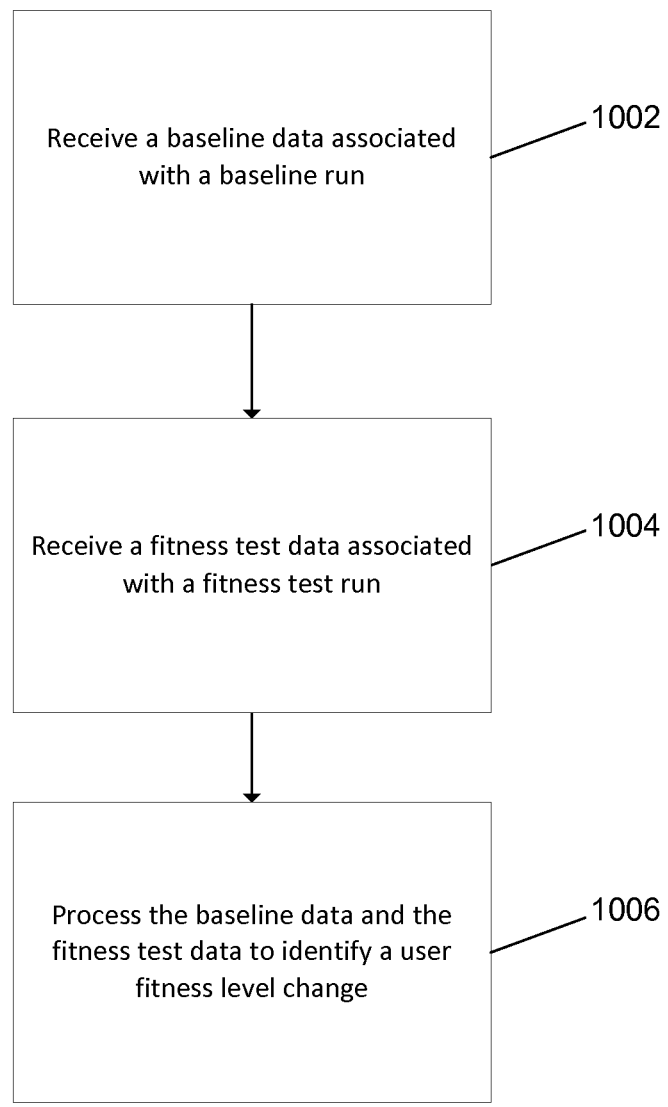
FIG. 10 is a flow diagram illustrating a method for fitness level monitoring in one example.

FIG. 10 is a flow diagram illustrating a method for fitness level monitoring in one example. At block 1002, a baseline data associated with a baseline run is received, the baseline data comprising a navigation data, a heart rate data, and a pace data. At block 1004, a fitness test data associated with a fitness test run is received. At block 1006, the baseline data and the fitness test data is processed to identify a user fitness level change. In one example, the user fitness level change is an improved fitness level.

In one example, the method further includes receiving a training data associated with a plurality of training runs, and processing the training data to identify a need for a fitness test run. In one example, the method further includes receiving a current training pace input by a user, wherein the user is prompted to run the baseline run at the current training pace.

In one example, the method further includes determining an updated current fitness level training pace. For example, an updated current fitness level training pace is determined by retrieving the heart rate data from the baseline data, receiving an update data associated with an update run, wherein during the update run the user is prompted to maintain a target heart rate, the target heart rate determined from the heart rate data from the baseline data, and processing the update data to determine an updated current training pace.

Figure 11:
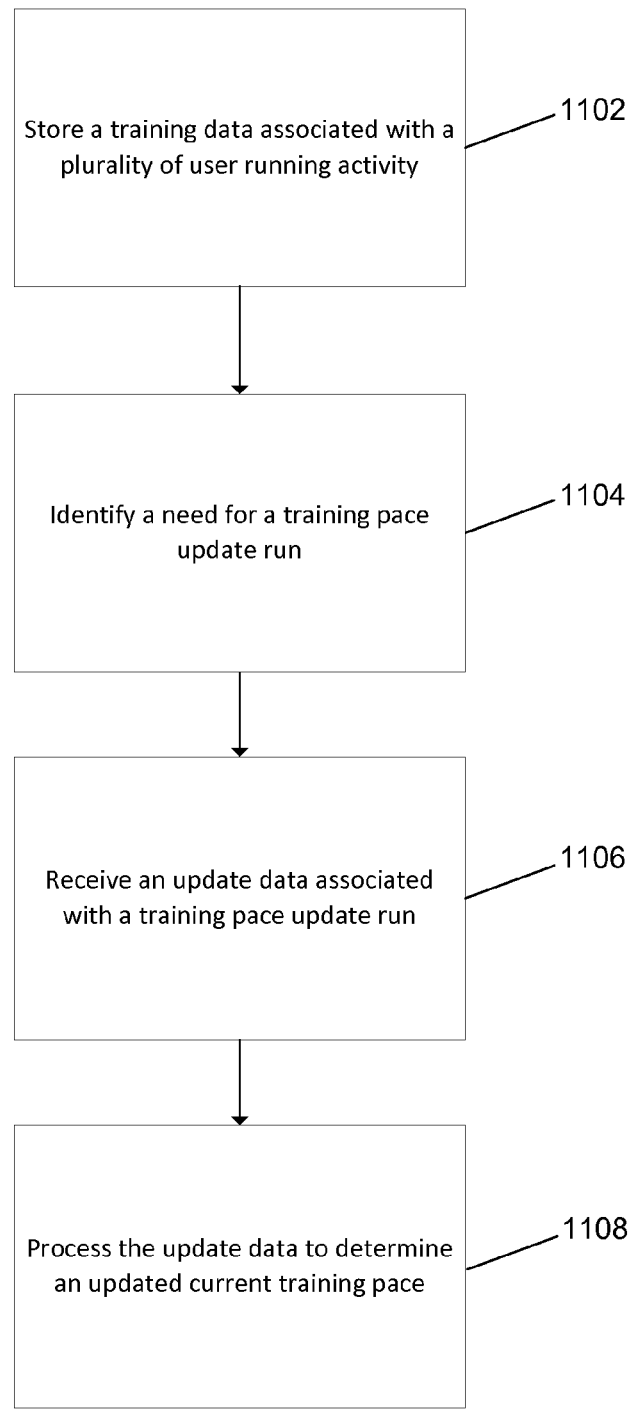
FIG. 11 is a flow diagram illustrating a method for updating a current training pace in one example.

FIG. 11 is a flow diagram illustrating a method for updating a current training pace in one example. At block 1102, a training data associated with a plurality of user running activity is stored, the training data comprising navigation data, heart rate data, and pace data.

At block 1104, a need for a training pace update run is identified. In one example, identifying a need for a training pace update run includes determining an elapsed time from a previous training pace update run. In one example, identifying a need for a training pace update run includes determining a user fitness level change. For example, determining a user fitness level change includes receiving a workout data associated with a workout running activity, and processing the workout data and the training data to determine a user fitness level change. Processing the workout data and the training data includes identifying a running activity from the training data having a same navigation route and a same approximate pace as the workout running activity, and comparing a first heart rate data associated with the running activity and a second heart rate data associated with workout running activity.

At block 1106, an update data associated with a training pace update run is received. In one example, during the training pace update run the user is prompted to maintain a target heart rate. For example, the target heart rate is determined from training data associated with a running activity in the plurality of user running activity.

At block 1108, the update data is processed to determine an updated current training pace. In one example, the method further includes receiving a data associated with a confirmation training run, the data operable to confirm the updated current training pace.

In one example, the method further includes identifying a current start location of a user, searching the training data associated with a plurality of user running activity to identify a user running activity having a same start location as the current start location, and prompting the runner during the training pace update run to run a route corresponding to the user running activity having a same start location as the current start location. For example, prompting the runner during the training pace update run includes outputting turn by turn directions. For example, the turn by turn directions are voice communications output at a headset.

Figure 12:
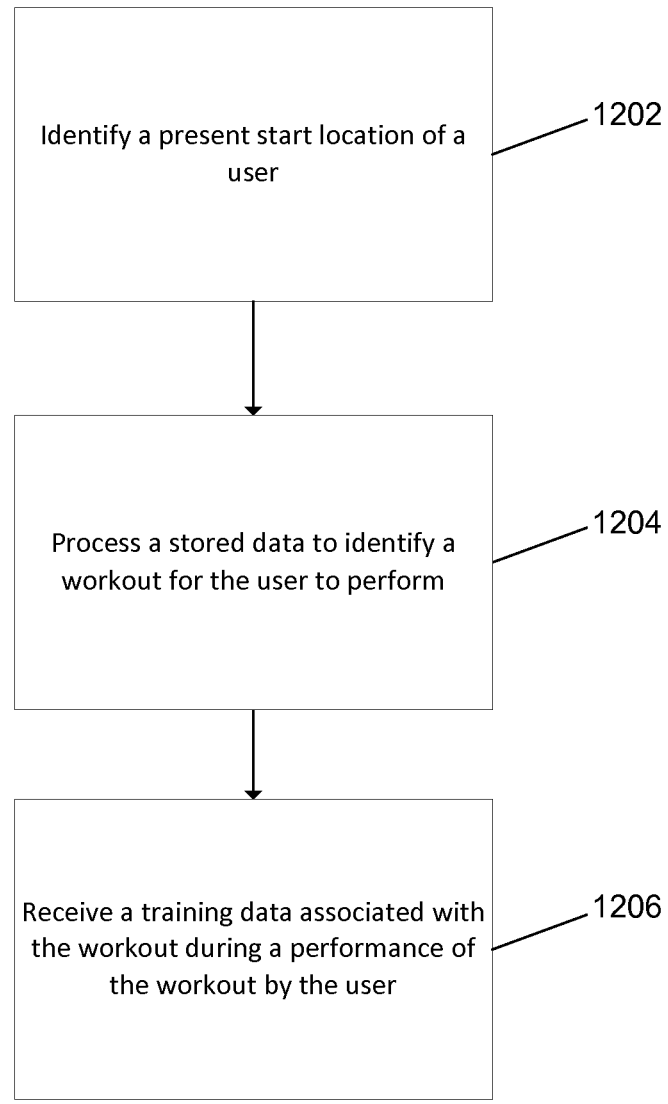
FIG. 12 is a flow diagram illustrating a method for athletic training in one example.

FIG. 12 is a flow diagram illustrating a method for athletic training in one example. At block 1202, a present start location of a user is identified.

At block 1204, a stored data is processed to identify a workout for the user to perform. In one example, processing a stored data to identify a workout for the user to perform utilizes the present start location of the user. In one example, the workout is a long run workout, interval workout, easy run workout, or tempo run workout. In one example, processing a stored data to identify a workout comprises identifying a plurality of workouts to present to the user from which the user may select.

In one example, processing a stored data to identify a workout comprises processing a stored training plan and identifying a most recent workout performed. In one example, the workout is obtained from a stored training plan which is web based such as a Google Calendar, Garmin Connect calendar. For example, the stored training plan may be previously posted by a Coach or pre-purchased by the user.

In one example, workouts are suggested to the user by a training optimization application based on one or more of the following criteria: (a) The user's current location (i.e., determined by GPS). For example, it is determined whether the user is currently at a track oval, a trail head appropriate for trail running, or at a location where the user has performed previous running activities, (b) The user's workout history (i.e., running activities stored in memory), including the most recent workout activity performed (e.g., 2 days ago, 1 week ago, etc.), workouts performed at the current location (e.g., workout type, duration, and intensity level (e.g., pace)), and (c) The current date and a training calendar (stored on either the device 2 or retrieved via a web interface (e.g., Garmin Connect or Google Calendar), etc.) providing workouts based on date, where the training optimization application 26 identifies a scheduled workout from the training calendar and selects a workout based on the user's current location and workout history. For example, where it is determined that the user is currently at a track oval and the workout history indicates the user did not perform the scheduled interval track workout as scheduled a few days ago, the training optimization application 26 may suggest this previously scheduled interval track workout instead of a currently scheduled workout (e.g., a tempo run). The suggested workout includes a workout type and pace information for example, and may be configured by training optimization application 26 so that the user is prompted appropriately during the workout (e.g., re: pace, heart rate, etc.) In one example, the training optimization application 26 selects the workout scheduled for the current day and configures the workout for the user, and the user selects and performs the workout as configured, (d) a pace update run is suggested if the training data indicates the user has not performed a pace update run recently (e.g., in the last 200 miles of running) Advantageously, in one example, training optimization application 26 automatically adapts the training plan based on actual user data.

At block 1206, a training data associated with the workout during a performance of the workout by the user is received. In one example, the training data comprises navigation data, heart rate data, and pace data.

In one example, the method further includes prompting the user during the workout with navigation data associated with the workout. In one example, the navigation data is generated from a web mapping interface such as Google Maps. In one example, the method further includes prompting the user during the workout with a target heart rate data associated with the workout.

In one example, the method further includes prompting the user during the workout with a target pace data associated with the workout. For example, the target pace data is a current updated pace determined from processing the stored data. In one example, the method further includes prompting the user during the workout with a target distance data associated with the workout.

Figure 13:
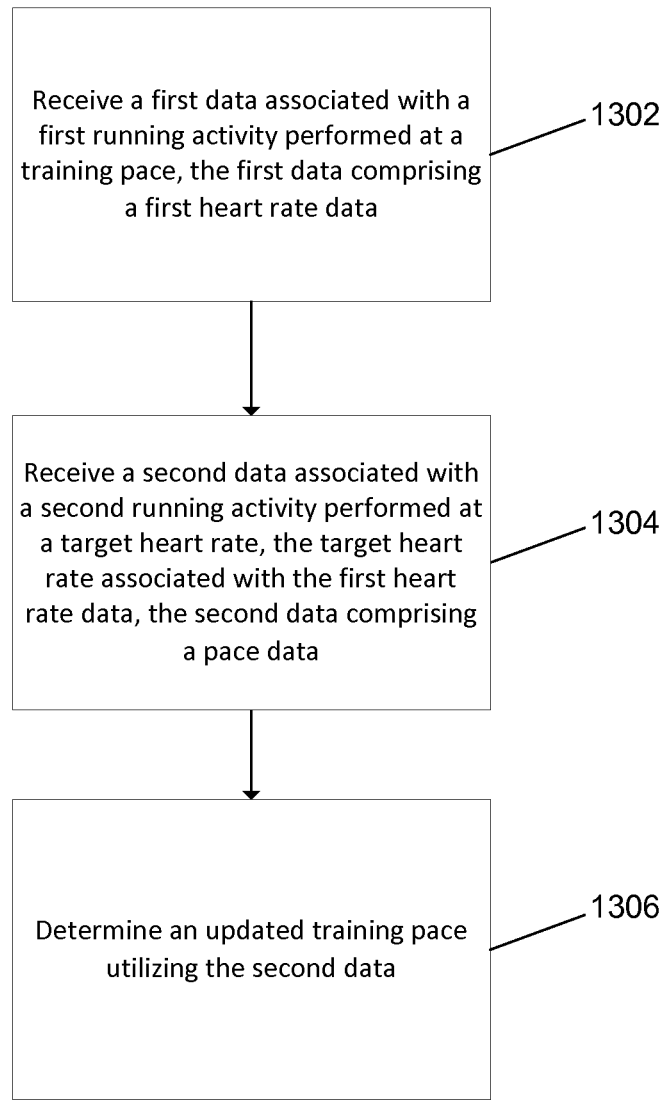
FIG. 13 is a flow diagram illustrating a method for athletic training in one example.

FIG. 13 is a flow diagram illustrating a method for athletic training in one example. At block 1302, a first data associated with a first running activity performed at a training pace is received, the first data comprising a first heart rate data. In one example, the training pace is a lactate threshold pace, marathon pace, half marathon pace, 10 k pace, 5 k pace, or base pace.

At block 1304, a second data associated with a second running activity performed at a target heart rate is received, the target heart rate associated with the first heart rate data, the second data comprising a pace data. At block 1306, an updated training pace utilizing the second data is determined. In one example, determining an updated current training pace utilizing the second data includes identifying an average pace.

Figure 14:
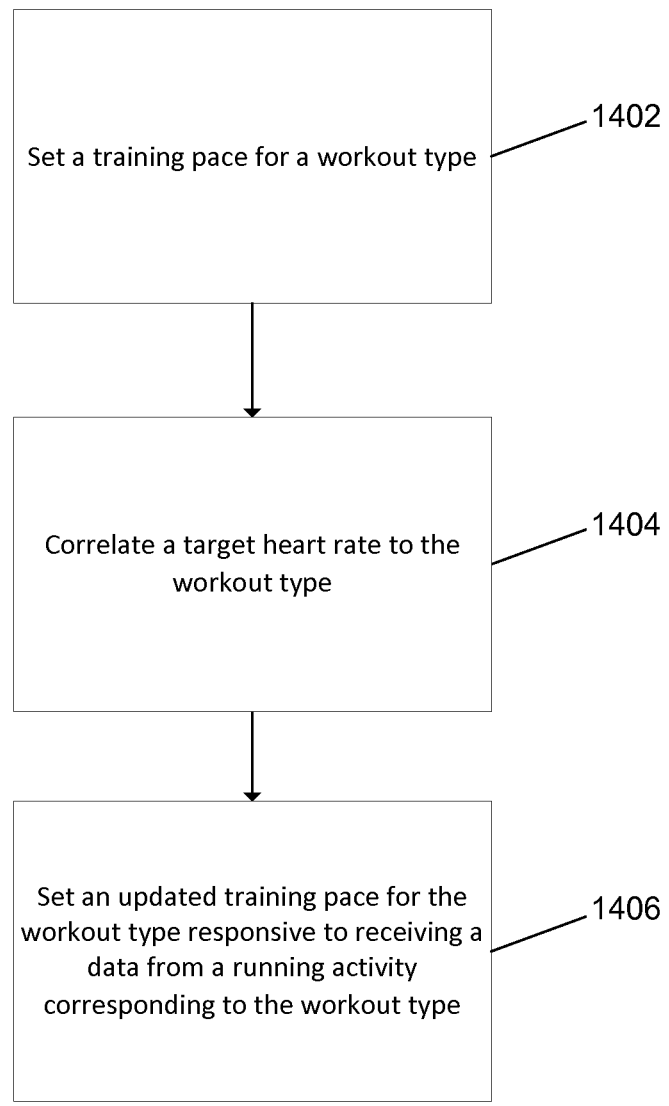
FIG. 14 is a flow diagram illustrating a method for athletic training in one example.

FIG. 14 is a flow diagram illustrating a method for athletic training in one example. At block 1402, a training pace for a workout type is set. In one example, the training pace is a base pace, interval pace, lactate threshold pace, or marathon pace. In one example, the workout type is a long run, a tempo run, a threshold run, or an interval.

At block 1404, a target heart rate is correlated to the workout type. In one example, correlating a target heart rate to the workout type includes utilizing data received from an activity performed at the training pace. In one example, the correlation between the target heart rate to the workout type is associated with an identified course.

At block 1406, an updated training pace for the workout type is set responsive to receiving a data from a running activity corresponding to the workout type. In one example, the running activity corresponding to the workout type is performed at the target heart rate.

Figure 15:
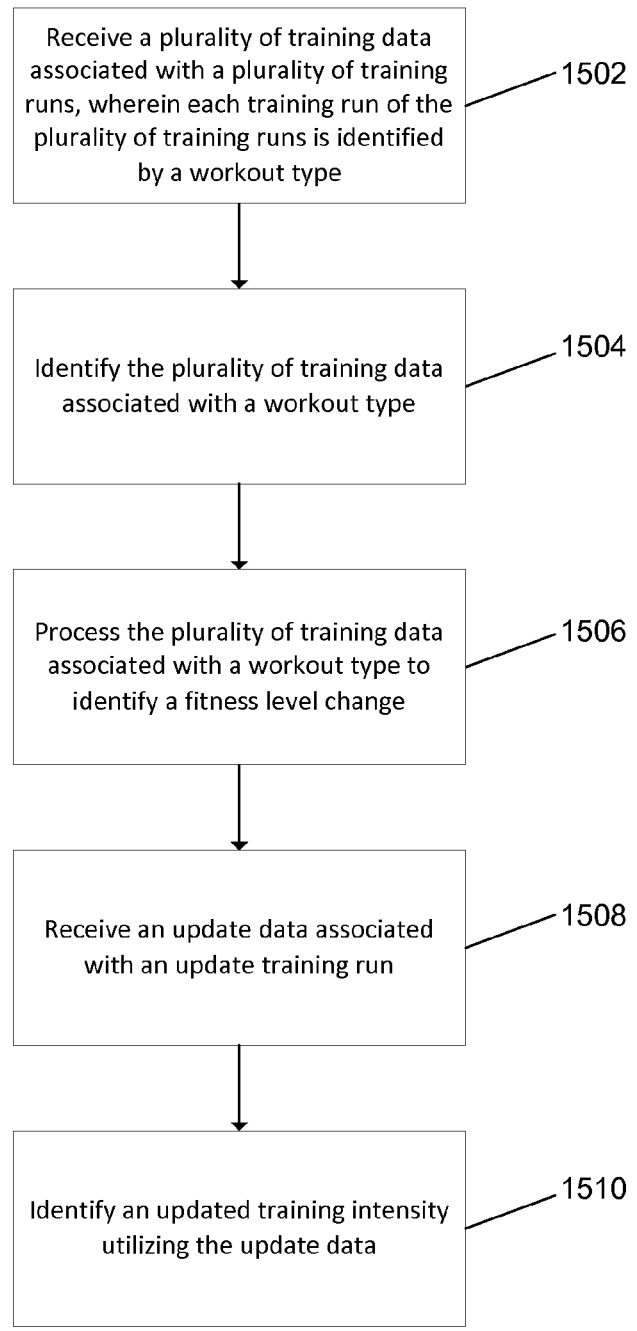
FIG. 15 is a flow diagram illustrating a method for athletic training in one example.

FIG. 15 is a flow diagram illustrating a method for athletic training in one example. At block 1502, a plurality of training data associated with a plurality of training runs is received, wherein each training run of the plurality of training runs is identified by a workout type. In one example, each training run is further identified by a course location.

At block 1504, the plurality of training data associated with a workout type is identified. At block 1506, the plurality of training data associated with a workout type is processed to identify a fitness level change. In one example, the user may be prompted to perform an update training run.

At block 1508, an update data associated with an update training run is received. At block 1510, an updated training intensity (e.g., training pace) is identified utilizing the update data. In one example, the updated training pace corresponds to a first workout type, the method further includes determining a second updated training pace corresponding to a second workout type.

In one example, the method further includes receiving a data associated with a confirmation training run, the data operable to confirm the updated training pace. In one example, the update training run is a first workout type and the confirmation training run is a second workout type. In one example, the data includes a heart rate data, the method further including outputting an alert during the confirmation training run if the heart rate exceeds a pre-determined maximum permissible rate.

Figure 16:
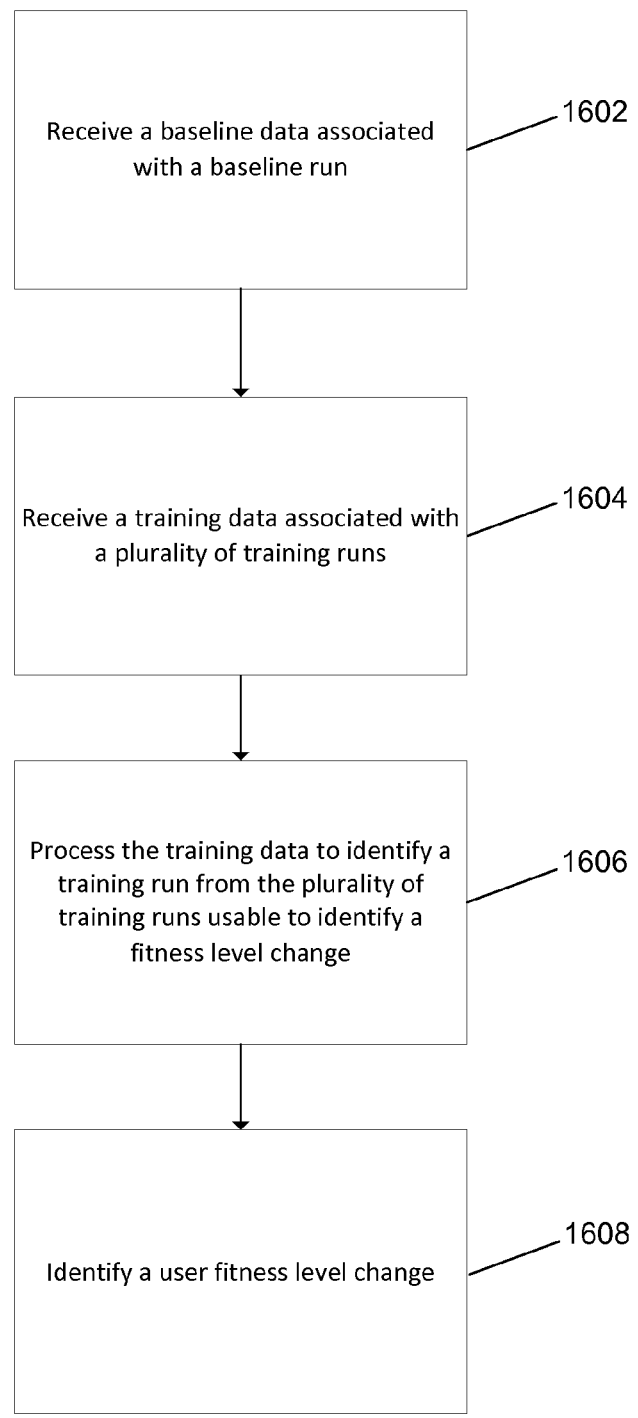
FIG. 16 is a flow diagram illustrating a method for fitness level monitoring in one example.

FIG. 16 is a flow diagram illustrating a method for fitness level monitoring in one example. At block 1602, a baseline data associated with a baseline run is received, the baseline data comprising a navigation data, a heart rate data, and a pace data. At block 1604, a training data associated with a plurality of training runs is received.

At block 1606, the training data is processed to identify a training run from the plurality of training runs usable to identify a fitness level change. In one example, processing the training data to identify a training run includes identifying a training run performed at a same pace as the baseline run. In one example, processing the training data to identify a training run includes identifying a training run performed at a same pace and a same course as the baseline run. At block 1608, a user fitness level change is identified.

Figure 17:
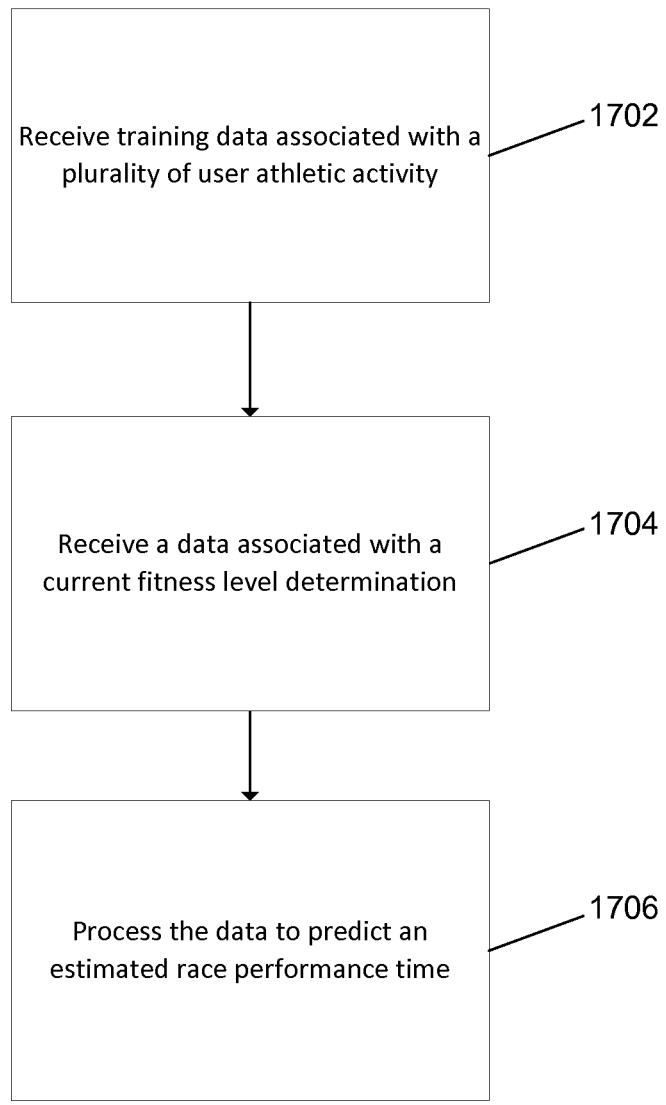
FIG. 17 is a flow diagram illustrating a method for predicting a race time in one example.

FIG. 17 is a flow diagram illustrating a method for predicting a race time in one example. At block 1702, a training data associated with a plurality of user athletic activity is received, the training data comprising navigation data, heart rate data, and pace data. At block 1704, a data associated with a current fitness level determination is received. At block 1706, the data associated with a current fitness level determination is processed to predict an estimated race performance time. The estimated race performance time is provided to the user and/or automatically used to configure a race activity to be performed by the user during the race. An estimated race performance time is useful to the athlete as it can be used to determine a pacing strategy for the race, providing an estimate of how slow or fast the user should begin the race. For example, for a half marathon race, the estimated race performance time is used to calculate an average pace for which the runner must run throughout the 13.1 miles in order to complete the 13.1 miles in the estimated race performance time. In one example, training optimization application 26 may configure a pacing strategy for the upcoming race for the runner to execute during the race. For example, in the simplest example, training optimization application 26 may configure the device 2 to prompt the user to maintain this determined average pace throughout the race (e.g., using the virtual pacer function or alerts if the user pace deviates from this pace by more than a threshold). In further examples, other pacing strategies may be developed from this determined average pace. In one example, the current fitness level determination is a training pace update activity. In one example, the method further includes identifying a need for a training pace update activity Instructions of the various software/firmware applications performing methods and functionality discussed herein are loaded for execution on a corresponding control unit or processor. The control unit or processor may include a microcontroller, a microprocessor, a processor module, or subsystem including one or more microprocessors and microcontrollers, or other control or computing devices. The term controller refers to either software or hardware, or a combination of both, and may refer to multiple software or hardware modules.

While the exemplary embodiments of the present invention are described and illustrated herein, it will be appreciated that they are merely illustrative and that modifications can be made to these embodiments without departing from the spirit and scope of the invention. For example, where a user "pace" is referred to, a user "speed" can be substituted. Any determination made by the systems and applications described herein can be output to the user via a device user interface for review. In certain examples, a running athletic activity is described though the discussed method may be utilized in other athletic activities such as swimming, cycling, etc. in further examples. Methods, techniques, and apparatuses described as applying to one embodiment or example may also be utilized with other embodiments or examples described herein. Thus, the scope of the invention is intended to be defined only in terms of the following claims as may be amended, with each claim being expressly incorporated into this Description of Specific Embodiments as an embodiment of the invention.

What is claimed is:

1. An apparatus comprising:
a processor;
a user interface;
an interface configured to receive a heart rate data from a heart rate monitor;
a navigation system configured to monitor a user navigation data comprising user location data and user speed data; and
a memory storing an application comprising instructions executable by the processor, the application configured to output a plurality of prompts at the user interface during an athletic activity, the plurality of prompts configured to assist in determining an updated current training intensity at which to perform a subsequent athletic activity, wherein the application is further configured to determine the updated current training intensity from a training data monitored during the athletic activity.

2. The apparatus of claim 1, wherein the application is further configured to output at the user interface the updated current training intensity upon completion of the athletic activity.

3. The apparatus of claim 1, wherein the plurality of prompts comprise prompts to maintain, increase, or decrease a user heart rate.

4. The apparatus of claim 1, wherein the plurality of prompts comprise prompts to maintain, increase, or decrease a user heart rate, and prompts to maintain, increase, or decrease a user intensity.

5. The apparatus of claim 1, wherein the updated current training intensity is a current lactate threshold pace at a time the athletic activity is performed.

6. The apparatus of claim 1, wherein the plurality of prompts are associated with a course location.

7. One or more non-transitory computer-readable storage media having computer-executable instructions stored thereon which, when executed by one or more computers, cause the one or more computers to perform operations comprising:

receiving a training data associated with a plurality of user athletic activity, the training data comprising a heart rate data and an intensity data;

receiving an update athletic activity data associated with a training intensity update athletic activity, the update athletic activity data comprising an update athletic activity heart rate data and an update athletic activity intensity data; and identifying an updated current training intensity at which to perform a subsequent athletic activity utilizing the update athletic activity data, the updated current training intensity corresponding to a current user fitness level at a time the training intensity update athletic activity is performed.

8. The one or more non-transitory computer-readable storage media of claim 7, wherein the operations further comprise identifying a need for the training intensity update athletic activity.

9. The one or more non-transitory computer-readable storage media of claim 8, wherein identifying the need for the training intensity update athletic activity comprises determining an elapsed time from a previous training intensity update athletic activity.

10. The one or more non-transitory computer-readable storage media of claim 8, wherein identifying the need for the training intensity update athletic activity comprises determining a user fitness level change.

11. The one or more non-transitory computer-readable storage media of claim 10, wherein determining the user fitness level change comprises:

receiving a workout data associated with a workout athletic activity; and determining the user fitness level change from the workout data and the training data.

12. The one or more non-transitory computer-readable storage media of claim 7, wherein during the training intensity update athletic activity a user is prompted to maintain a target heart rate.

13. The one or more non-transitory computer-readable storage media of claim 12, wherein the target heart rate is determined from training data associated with an athletic activity in the plurality of user athletic activity.

14. The one or more non-transitory computer-readable storage media of claim 7, wherein the training data further comprises a navigation data and the update athletic activity data further comprises an update athletic activity navigation data, and wherein the operations further comprise:

identifying a current start location of a user;

searching the training data associated with a plurality of user athletic activity to identify a user athletic activity having a same start location as the current start location; and prompting the user during the training intensity update athletic activity to follow a route corresponding to the user athletic activity having a same start location as the current start location.

* * * * *